United States Patent
Egawa

(10) Patent No.: US 8,911,882 B2
(45) Date of Patent: Dec. 16, 2014

(54) STILBENE DERIVATIVE, LIGHT-EMITTING ELEMENT, LIGHT-EMITTING DEVICE, AND ELECTRONIC DEVICE

(75) Inventor: Masakazu Egawa, Tochigi (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 448 days.

(21) Appl. No.: 11/858,544

(22) Filed: Sep. 20, 2007

(65) Prior Publication Data

US 2008/0088229 A1    Apr. 17, 2008

(30) Foreign Application Priority Data

Sep. 28, 2006    (JP) .................................. 2006-265207

(51) Int. Cl.
H01L 51/54    (2006.01)
C09K 11/06    (2006.01)

(52) U.S. Cl.
CPC ................ *C09K 11/06* (2013.01); *H02B 33/14* (2013.01); *C09K 2211/1007* (2013.01); *C09K 2211/1011* (2013.01); *C09K 2211/1014* (2013.01); *C09C 211/54* (2013.01); *Y10S 428/917* (2013.01)
USPC ............ 428/690; 428/917; 313/504; 313/506

(58) Field of Classification Search
CPC .................. C07C 211/54; C09K 11/06; C09K 2211/1011; C09K 211/1014; C09K 2211/1007; H05B 33/14; H01L 51/50
See application file for complete search history.

(56) References Cited

U.S. PATENT DOCUMENTS 4,666,810 A    5/1987    Umehara et al.
4,808,503 A *  2/1989    Yamada et al. ................ 430/75

(Continued)

FOREIGN PATENT DOCUMENTS

CN    1292022 A    4/2001
EP    1 061 112 A1  12/2000

(Continued)

OTHER PUBLICATIONS

English translation of Suzuki et al., JP 04361269, which was published Dec. 1992.*

(Continued)

*Primary Examiner* — Dawn L. Garrett
(74) *Attorney, Agent, or Firm* — Husch Blackwell LLP

(57) ABSTRACT

The present invention provides a novel organic compound having excellent heat resistance. By using the novel organic compound, a light-emitting element and a light-emitting device which have excellent heat resistance can be provided. A stilbene derivative expressed by the general formula (1) is provided. Since the stilbene derivative expressed by the general formula (1) has high glass transition point, when it is used for a light-emitting element, the light-emitting element, and a light-emitting device using the light-emitting element which have excellent heat resistance can be obtained. Further, since the stilbene derivative expressed by the general formula (1) has good light emission efficiency; therefore, when it is used for a light emitting element, a light emitting element and a light emitting device which consumes less power can be obtained.

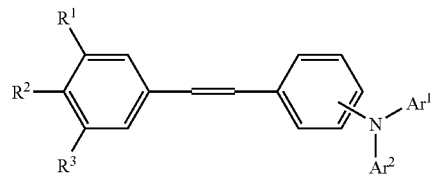

(1)

15 Claims, 13 Drawing Sheets

(56) References Cited

U.S. PATENT DOCUMENTS

| | | | |
|---|---|---|---|
| 4,859,556 A | | 8/1989 | Sasaki |
| 4,892,949 A | | 1/1990 | Sasaki |
| 5,073,465 A | * | 12/1991 | Makino et al. ............ 430/59.3 |
| 5,085,946 A | | 2/1992 | Saito et al. |
| 5,232,800 A | * | 8/1993 | Pavlisko et al. .......... 430/59.6 |
| 5,281,489 A | * | 1/1994 | Mori et al. ................. 428/690 |
| 5,550,000 A | * | 8/1996 | Takegawa et al. ........ 430/131 |
| 6,046,348 A | * | 4/2000 | Yamada et al. ........... 556/413 |
| 6,066,712 A | * | 5/2000 | Ueda et al. ................. 528/244 |
| 6,468,675 B1 | | 10/2002 | Ishikawa et al. |
| 6,653,034 B2 | * | 11/2003 | Inagaki et al. .......... 430/58.15 |
| 6,743,948 B1 | | 6/2004 | Hosokawa et al. |
| 6,951,693 B2 | | 10/2005 | Hosokawa et al. |
| 7,122,256 B2 | | 10/2006 | Funahashi et al. |
| 7,476,745 B2 | * | 1/2009 | Egawa et al. ............... 548/440 |
| 7,598,667 B2 | | 10/2009 | Kawamura et al. |
| 7,638,663 B2 | | 12/2009 | Egawa et al. |
| 7,732,619 B2 | | 6/2010 | Egawa et al. |
| 7,898,171 B2 | * | 3/2011 | Egawa et al. ............... 313/504 |
| 7,935,854 B2 | | 5/2011 | Egawa et al. |
| 8,134,148 B2 | | 3/2012 | Egawa et al. |
| 8,193,701 B2 | * | 6/2012 | Egawa et al. ............... 313/504 |
| 2003/0072966 A1 | | 4/2003 | Hosokawa et al. |
| 2003/0222575 A1 | | 12/2003 | Yamazaki et al. |
| 2005/0038296 A1 | | 2/2005 | Hosokawa et al. |
| 2005/0214565 A1 | | 9/2005 | Ikeda et al. |
| 2005/0238912 A1 | | 10/2005 | Funahashi et al. |
| 2006/0189828 A1 | | 8/2006 | Hosokawa et al. |
| 2007/0080630 A1 | | 4/2007 | Egawa et al. |
| 2007/0142671 A1 | | 6/2007 | Hosokawa et al. |
| 2008/0091030 A1 | | 4/2008 | Egawa et al. |
| 2009/0146558 A1 | * | 6/2009 | Egawa et al. ............... 313/504 |
| 2010/0160687 A1 | | 6/2010 | Hosokawa et al. |
| 2012/0235130 A1 | | 9/2012 | Egawa et al. |

FOREIGN PATENT DOCUMENTS

| | | | |
|---|---|---|---|
| EP | 1 314 715 A1 | | 5/2003 |
| EP | 1 623 970 A1 | | 2/2006 |
| EP | 1 666 561 A1 | | 6/2006 |
| EP | 1 775 335 A2 | | 4/2007 |
| JP | 62-18565 | | 1/1987 |
| JP | 2-291696 | | 12/1990 |
| JP | 4-361269 | * | 12/1992 |
| JP | 5-295359 | | 11/1993 |
| JP | 08-283708 | * | 10/1996 |
| JP | 2001-126873 | | 5/2001 |
| JP | 2004-35447 | | 2/2004 |
| JP | 2004-75580 | | 3/2004 |
| JP | 2004-196716 | | 7/2004 |
| WO | WO 00/39247 A1 | | 7/2000 |
| WO | WO 02/20459 A1 | | 3/2002 |
| WO | WO 02/20694 A1 | | 3/2002 |
| WO | WO 2004/101491 | | 11/2004 |

OTHER PUBLICATIONS

Machine generated translation for JP 08-283708, which was published Oct. 1996.*

Cha, S.W. et al, "Electroluminescence of LEDs Consisting Two Layers of $Alq_3$ and High $T_g$, Blue-Light Emitting Branched Compounds," Synthetic Metals, vol. 143, 2004, pp. 97-101.

Office Action re Chinese application No. CN 200710161325.8, dated May 31, 2011 (with English translation).

Thelakkat, M. et al, "Novel Functional Materials Based on Triarylamines-Synthesis and Application in Electroluminescent Devices and Photorefractive Systems," Phys. Chem. Chem. Phys., vol. 1, No. 8, Apr. 15, 1999, pp. 1693-1698.

* cited by examiner

STILBENE DERIVATIVE, LIGHT-EMITTING ELEMENT, LIGHT-EMITTING DEVICE, AND ELECTRONIC DEVICE

BACKGROUND OF THE INVENTION

1. Field of the Invention

The present invention relates to stilbene derivatives, and light-emitting elements, light-emitting devices, electronic devices which use the stilbene derivatives.

2. Description of the Related Art

Organic compounds can take more various structures compared with inorganic compounds, and have possibility to provide materials having various functions by appropriate molecular design. Due to these advantages, photo electronics and electronics which utilize functional organic materials have been attracting attention in recent years.

For example, a solar cell, a light-emitting element, an organic transistor, and the like are exemplified as electronic devices utilizing an organic compound as a functional organic material. These devices utilize electric properties and optical properties of the organic compound. Among them, in particular, a light-emitting element has been making remarkable development.

It is said that light emission mechanism of a light-emitting element is as follows: when a voltage is applied between a pair of electrodes with a light-emitting layer interposed therebetween, electrons injected from a cathode and holes injected from an anode are recombined in the light emission center of the light-emitting layer to form a molecular excitons, and energy is released to emit light when the molecular excitons return to a ground state. As excited states, a singlet excited state and a triplet excited state are known, and light emission is considered to be obtained from any of these excited states.

Such a light-emitting element has a lot of problems which depend on materials, in improving the element characteristics. In order to solve these problems, improvement of an element structure, development of a material, and the like have been carried out.

For example, Japanese Published Patent Application No. H2-291696 (Reference 1) discloses a stilbene derivative formed by combining stilbene and amine.

SUMMARY OF THE INVENTION

However, it is considered that properties such as heat resistance of a stilbene derivative disclosed in Reference 1, in which stilbene and amine are combined, are not sufficiently high.

It is an object of the present invention to provide a novel organic compound having excellent heat resistance.

It is another object of the present invention to provide an organic compound having excellent heat resistance, which can be suitably used as a material of a light emitting element.

Further, a light-emitting element and a light-emitting device which have excellent heat resistance can be provided.

It is still another object to provide an electronic device having excellent heat resistance.

It is still another object to provide an organic compound having high light emission efficiency.

It is still another object to provide a light emitting element, a light emitting device, or an electronic device, which have high light emission efficiency.

It is still another object to provide an organic compound having high light emission efficiency in addition to high heat resistance.

It is still another object to provide a light emitting element, a light emitting device, or an electronic device which have high light emission efficiency.

An aspect of the present invention is a stilbene derivative represented by general formula (1).

(1)

In the general formula (1), $R^1$ to $R^3$ each represent a hydrogen atom or an alkyl group having 1 to 3 carbon atoms. Further, $Ar^1$ represents one of a substituted or unsubstituted biphenyl group and a substituted or unsubstituted terphenyl group, and $Ar^2$ represents one of a substituted or unsubstituted phenyl group, a substituted or unsubstituted biphenyl group, and a substituted or unsubstituted terphenyl group.

An aspect of the present invention is a stilbene derivative represented by the general formula (2).

(2)

(3)

(4)

In the general formula (2), $R^1$ to $R^3$ each represent a hydrogen atom or an alkyl group having 1 to 3 carbon atoms. Further, A represents a substituent expressed by the structural formula (3) or the structural formula (4). $Ar^2$ represents one of a substituted or unsubstituted phenyl group, a substituted or unsubstituted biphenyl group, and a substituted or unsubstituted terphenyl group.

An aspect of the present invention is a stilbene derivative represented by the general formula (5).

(5)

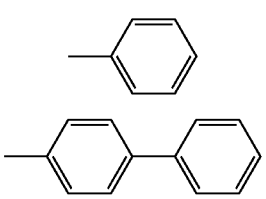

(6)

(7)

In the general formula (5), $R^1$ to $R^3$ each represent a hydrogen atom or an alkyl group having 1 to 3 carbon atoms. Further, A represents a substituent expressed by the structural formula (6) or the structural formula (7). B represents a hydrogen atom or a substituent expressed by the structural formula (6) or the structural formula (7).

An aspect of the present invention is a stilbene derivative represented by the general formula (8).

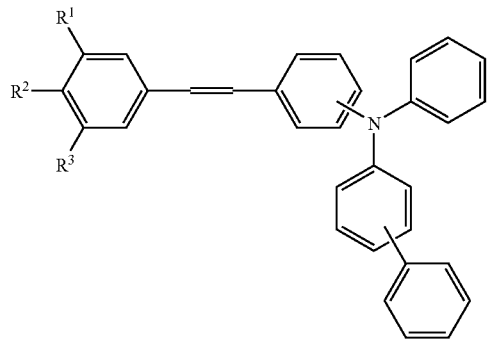

(8)

In the general formula (8), $R^1$ to $R^3$ each represent a hydrogen atom, or an alkyl group having 1 to 3 carbon atoms.

An aspect of the present invention is a stilbene derivative represented by structural formula (9) below.

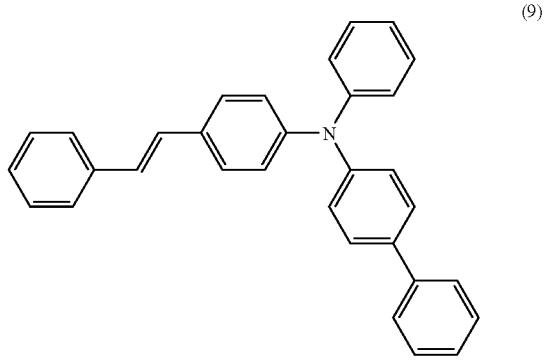 [SMILES: C(=C\c1ccc(N(c2ccccc2)c2ccc(-c3ccccc3)cc2)cc1)/c1ccccc1]

(9)

An aspect of the present invention is a light-emitting element using any one of the above stilbene derivatives. Specifically, a light-emitting element has any one of the above stilbene derivatives between a pair of electrodes.

An aspect of the present invention is a light-emitting element having a light-emitting layer between a pair of electrodes, and the light-emitting layer includes any of the above stilbene derivatives.

Moreover, a light-emitting device of the present invention has a light-emitting element including a light-emitting element containing any of the above stilbene derivatives between a pair of electrodes, and a controller for controlling light emission of the light-emitting element. It is to be noted that the light-emitting device in this specification includes an image display device, a light-emitting device, and a light source (including a lighting device). Further, the light-emitting device includes various types of modules e.g., a module in which a connector such as an FPC (Flexible Printed Circuit), a TAB (Tape Automated Bonding) tape, or a TCP (Tape Carrier Package) is attached to a panel, a module in which a print wiring board is provided at an end of a TAB tape or an TCP, and a module in which an IC (Integrated Circuit) is directly mounted on a light-emitting device by a COG (Chip On Glass) method.

Electronic devices each using the light-emitting element of the present invention in its display portion are also included in the category of the present invention. Therefore, electronic devices of the present invention each have a display portion provided with the aforementioned light-emitting element and a controller for controlling light emission of the light-emitting element.

A stilbene derivative of the present invention has excellent heat resistance. Further, a stilbene derivative of the present invention has good light emission efficiency.

Since a stilbene derivative of the present invention has excellent heat resistance, when it is used for a light-emitting element, the light-emitting element and a light-emitting device using the light-emitting element also have excellent heat resistance.

Moreover, since a stilbene derivative of the present invention has good light emission efficiency, when it is used for a light emitting element, a light emitting element and a light emitting device which consume less power can be obtained.

By using a stilbene derivative of the present invention, an electronic device having excellent heat resistance which consumes less power can be provided.

DETAILED DESCRIPTION OF THE INVENTION

Figure 1A:
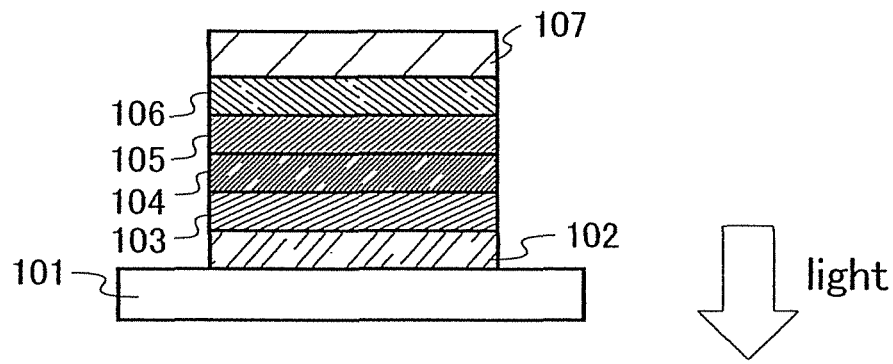
FIGS. 1A to 1C illustrate light-emitting elements of the present invention.

Embodiment modes and examples of the present invention will be described below with reference to the drawings in detail. Note that the present invention is not limited to the following description and it is easily understood by those skilled in the art that the mode and details can be variously changed without departing from the scope and spirit of the present invention. Therefore, the present invention is not construed as being limited to the description of the embodiment modes and examples shown below.

Embodiment Mode 1

A stilbene derivative of the present invention is expressed by the general formula (1).

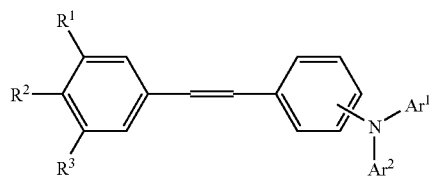
(1)

In the general formula (1), $R^1$ to $R^3$ each represent a hydrogen atom, or an alkyl group having 1 to 3 carbon atoms. Further, $Ar^1$ represents one of a substituted or unsubstituted biphenyl group and a substituted or unsubstituted terphenyl group, and $Ar^2$ represents one of a substituted or unsubstituted phenyl group, a substituted or unsubstituted biphenyl group, and a substituted or unsubstituted terphenyl group.

In the general formula (1), a biphenyl group having a substituent and a terphenyl group having a substituent, preferably have an alkyl group or a phenyl group as the substituents. As the alkyl group, a methyl group, an ethyl group, an n-propyl group, an iso-propyl group, an n-butyl group, an iso-butyl group, a sec-butyl group, a tert-butyl group, or the like can be used.

In particular, a stilbene derivative expressed by the general formula (2) is preferable.

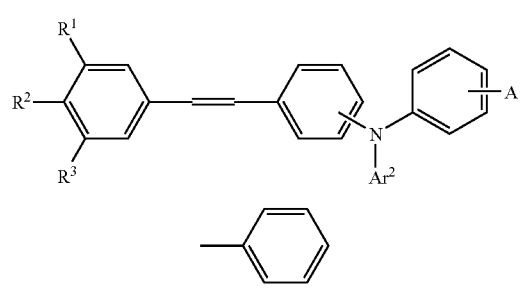
(2)

(3)

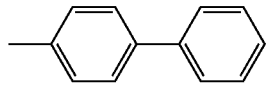
(4)

In the general formula (2), $R^1$ to $R^3$ each represent a hydrogen atom or an alkyl group having 1 to 3 carbon atoms. Further, A represents a substituent expressed by the structural formula (3) or the structural formula (4). $Ar^2$ represents one of a substituted or unsubstituted phenyl group, a substituted or unsubstituted biphenyl group, and a substituted or unsubstituted terphenyl group.

In particular, a stilbene derivative expressed by the general formula (5) is preferable.

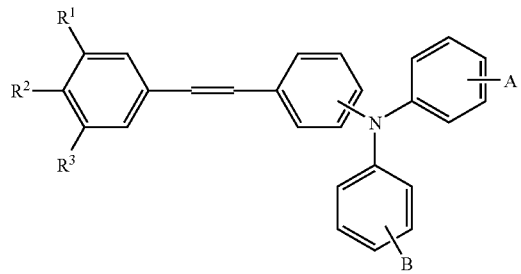
(5)

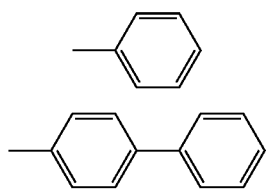
(6)

(7)

In the general formula (5), $R^1$ to $R^3$ each represent a hydrogen atom or an alkyl group having 1 to 3 carbon atoms. Further, A represents a substituent expressed by the structural formula (6) or the structural formula (7). B represents a hydrogen atom or a substituent expressed by the structural formula (6) or the structural formula (7).

In particular, a stilbene derivative expressed by the general formula (8) is preferable.

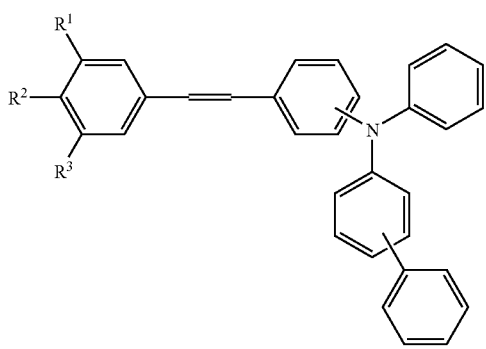
(8)

In the general formula (9), $R^1$ to $R^3$ each represent a hydrogen atom, or an alkyl group having 1 to 3 carbon atoms.

In particular, a stilbene derivative represented by the general formula (9) is preferable.

(9)
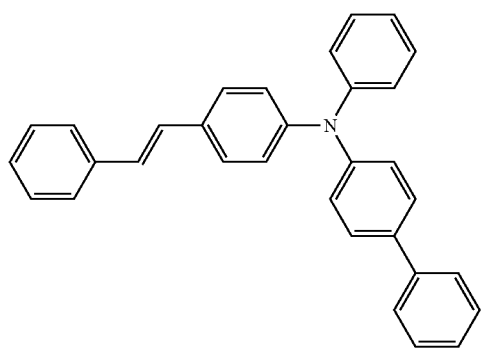
(13)
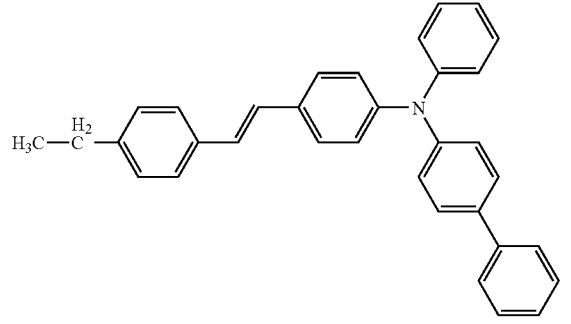
Specific examples of stilbene derivatives of the present invention can be stilbene derivatives expressed by the following structural formulas (10) to (61). However, the present invention is not limited to these examples.
(10)
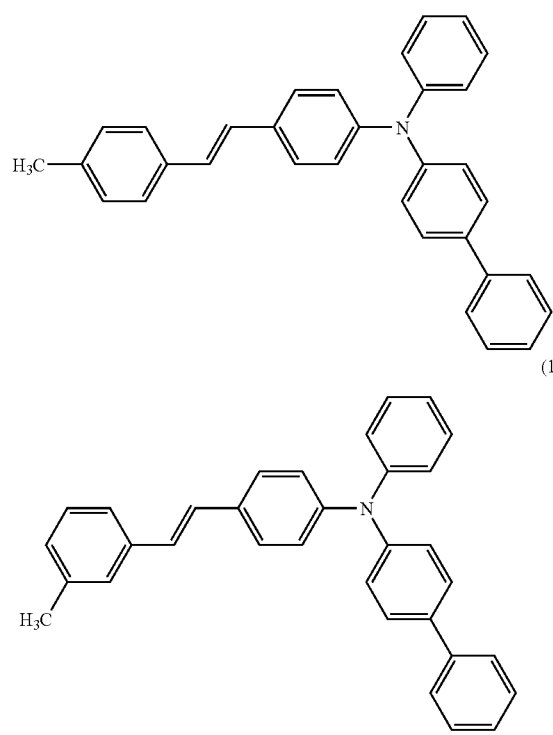
(14)
(11)
(15)
(12)
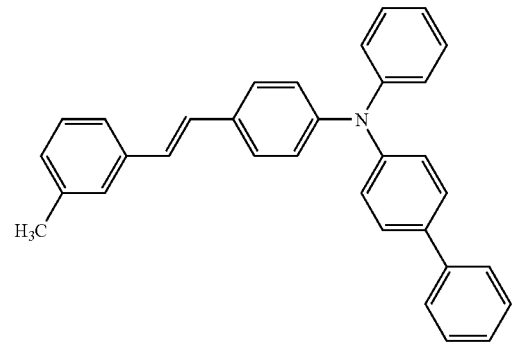
(16)
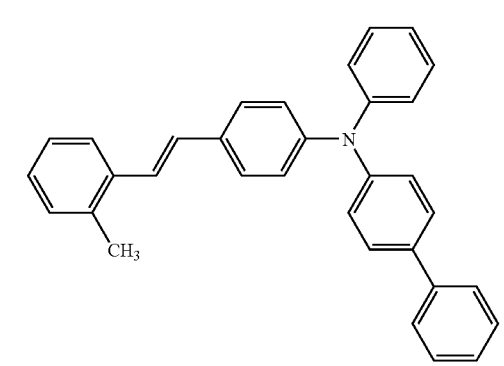

(17)
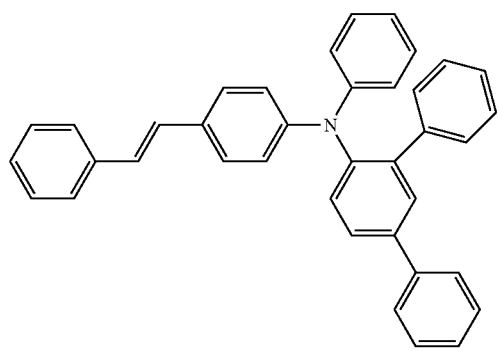
(18)
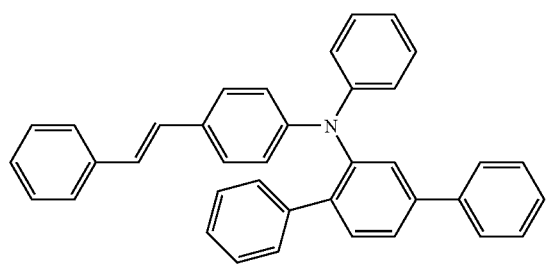
(19)
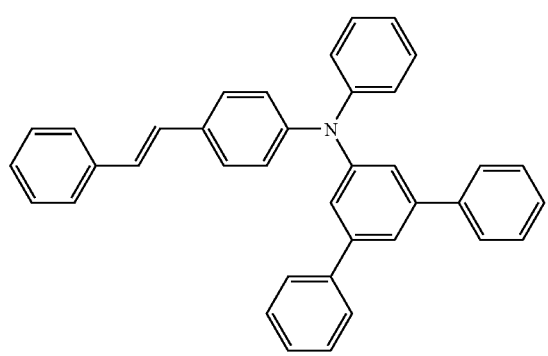
(20)
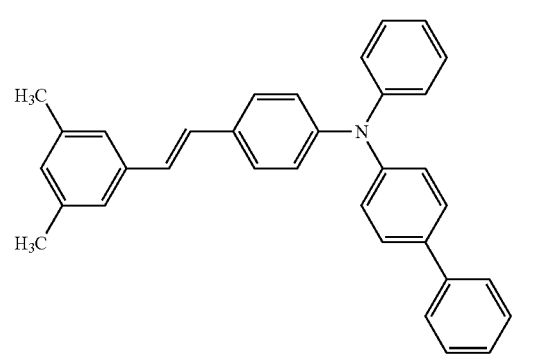
(21)
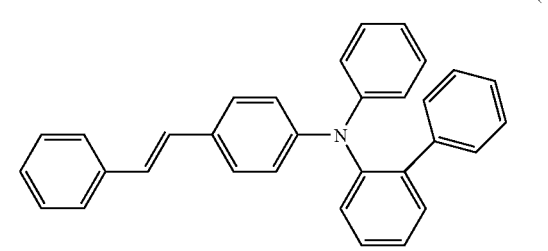
(22)
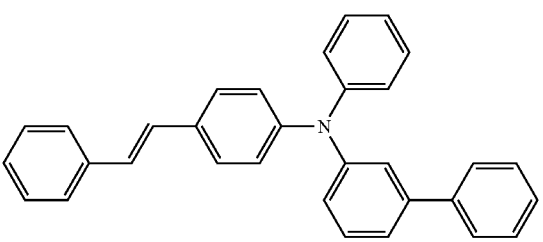
(23)
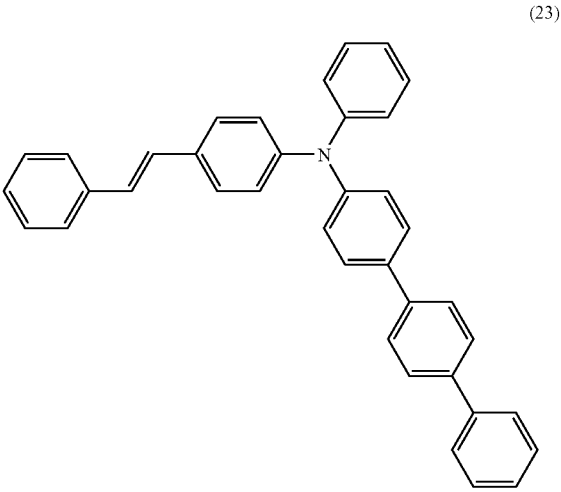
(24)
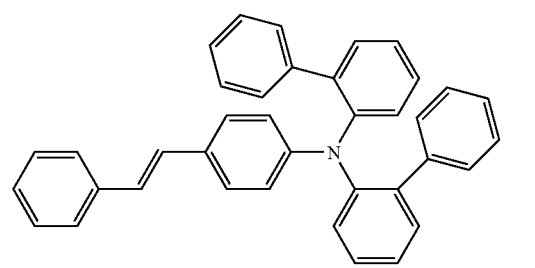
(25)
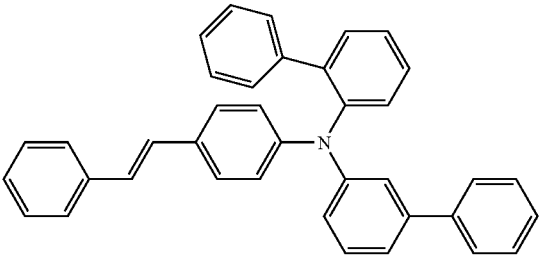

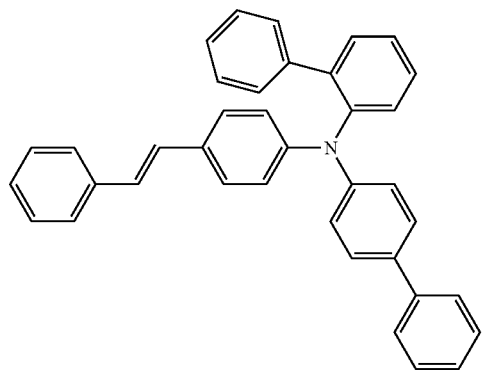
(26)
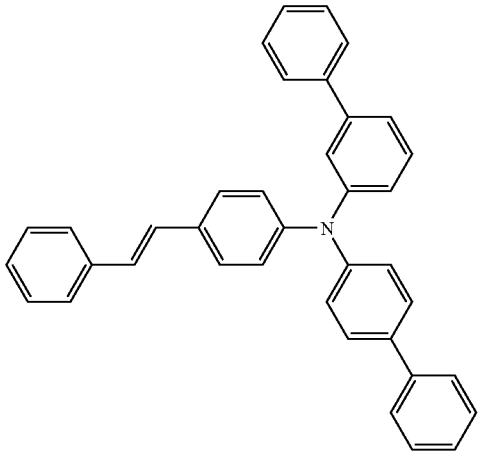
(29)
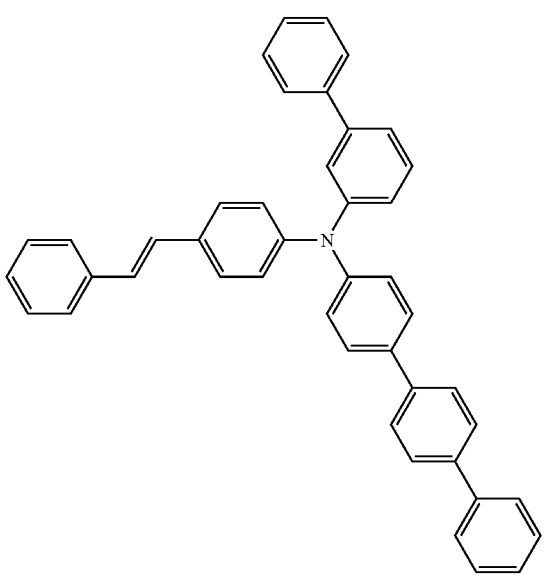
(27)
(30)
(28)
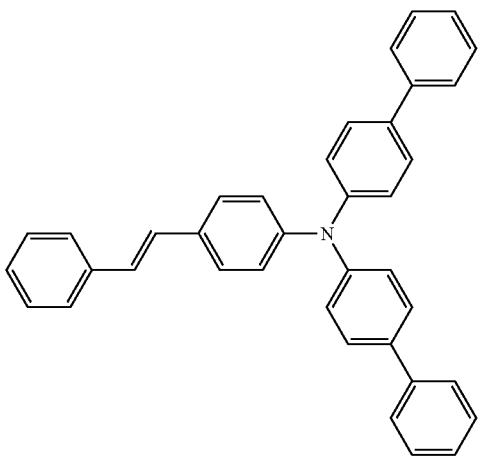
(31)

(32)
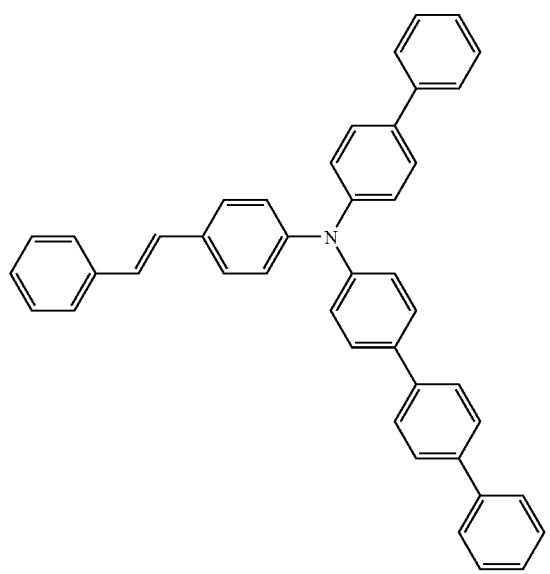
(33)
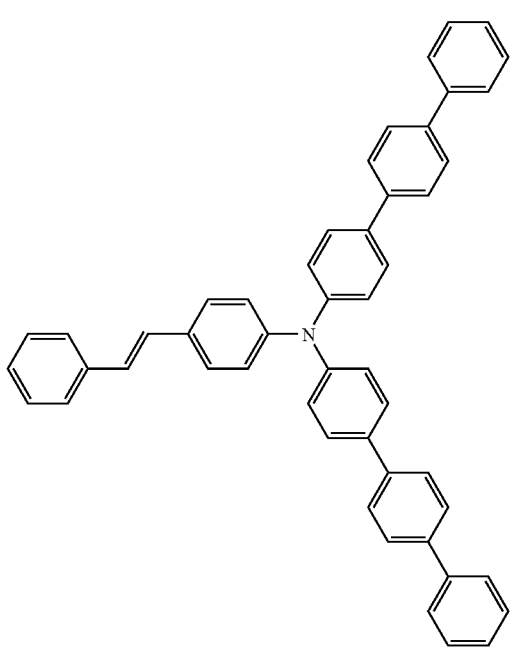
(34)
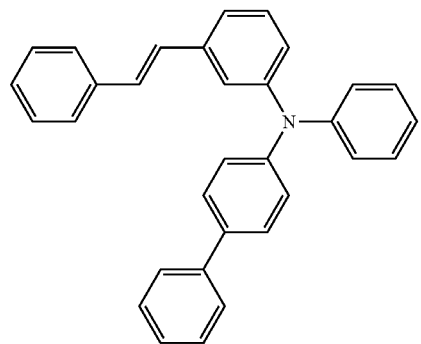
(35)
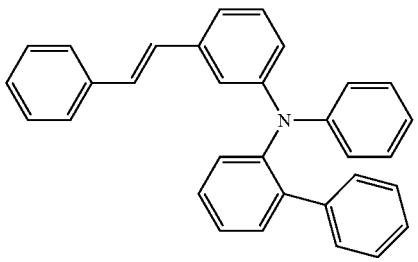
(36)
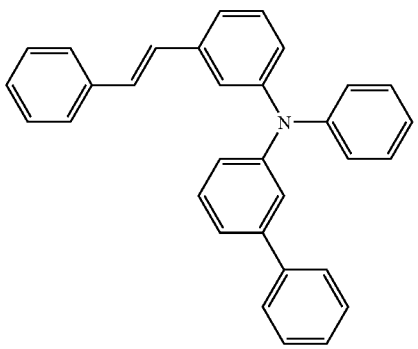
(37)
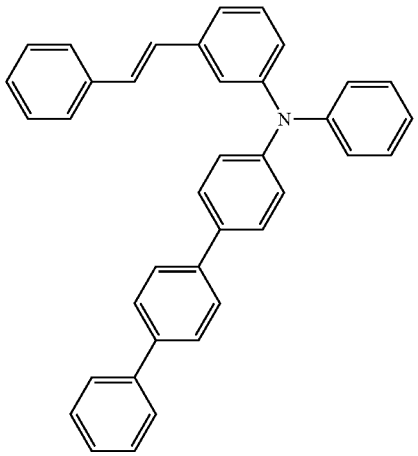
(38)
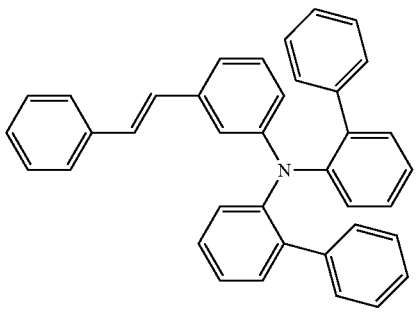

(39)
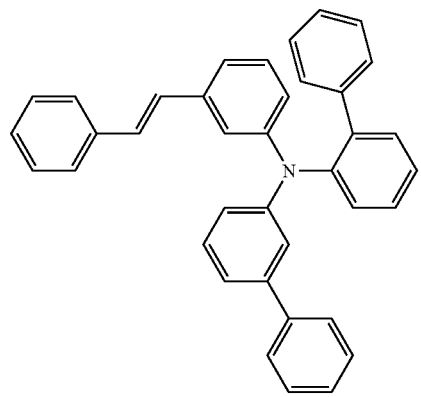
(40)
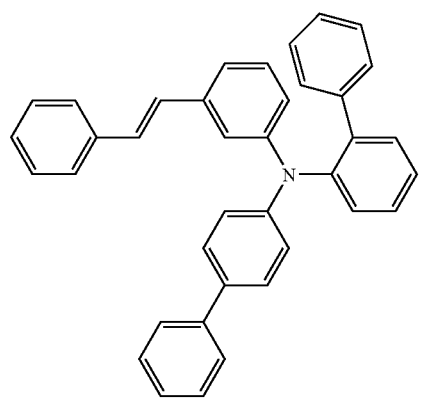
(41)
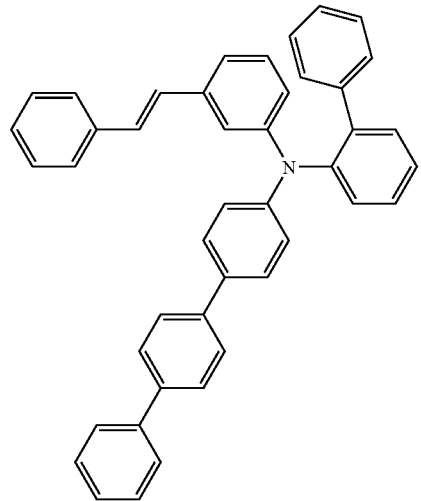
(42)
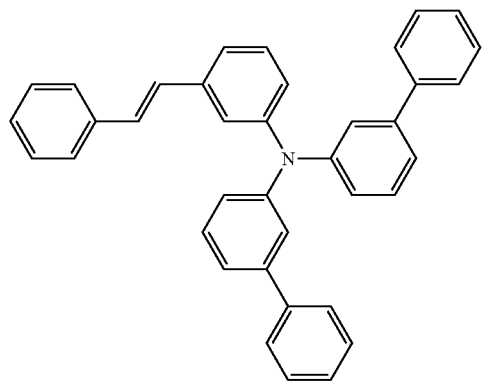
(43)
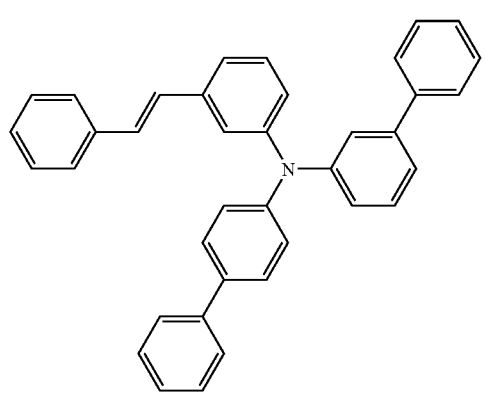
(44)
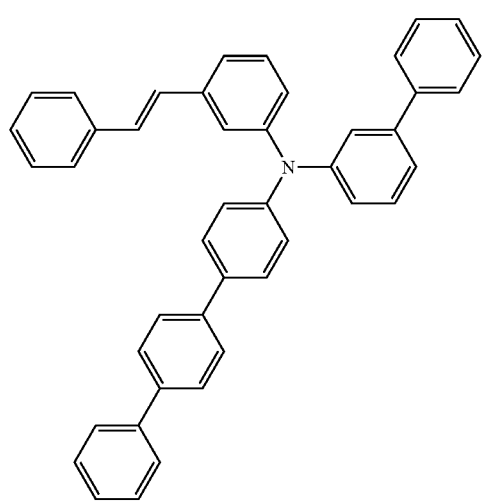
(45)
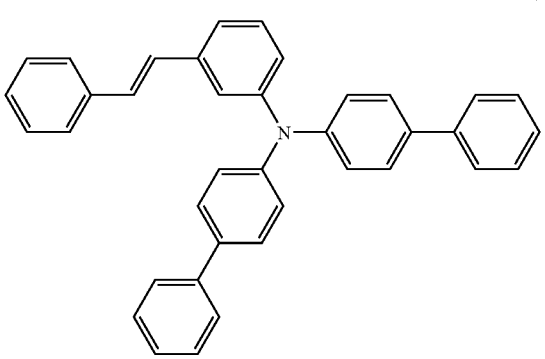

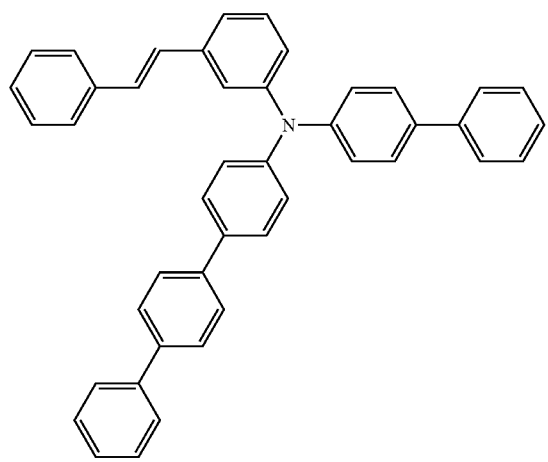
(46)
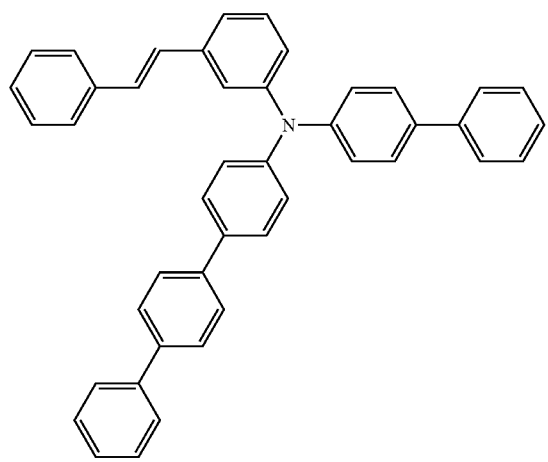
(47)
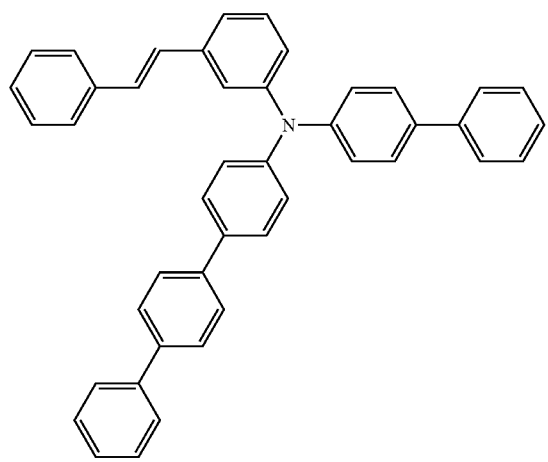
(48)
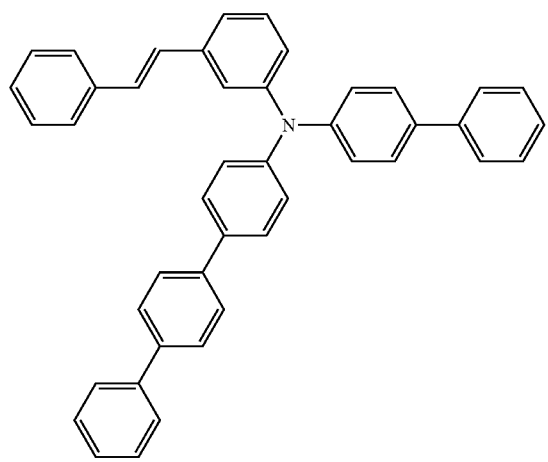
(49)
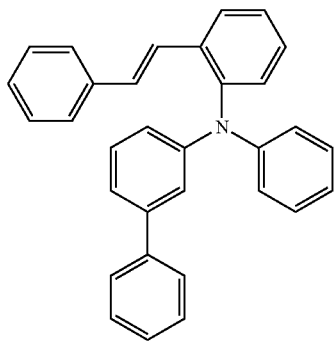
(50)
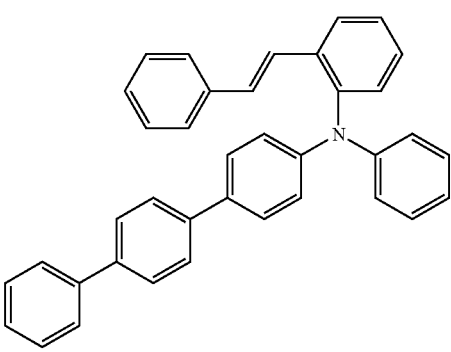
(51)
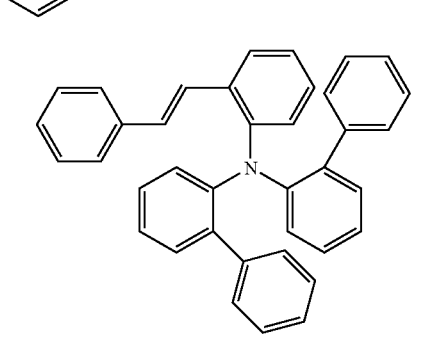
(52)
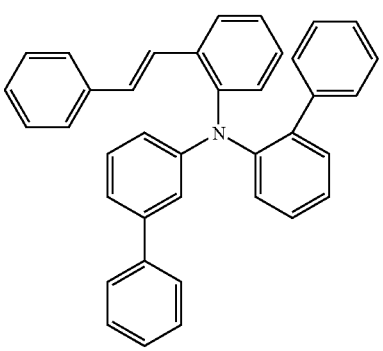
(53)
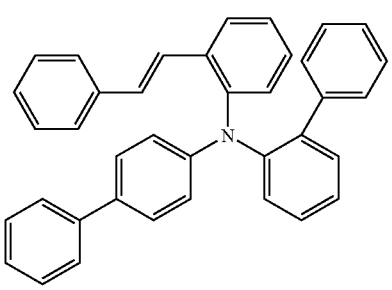
(54)

-continued

(55)
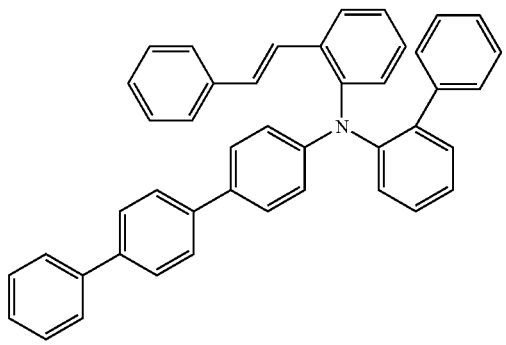

(56)
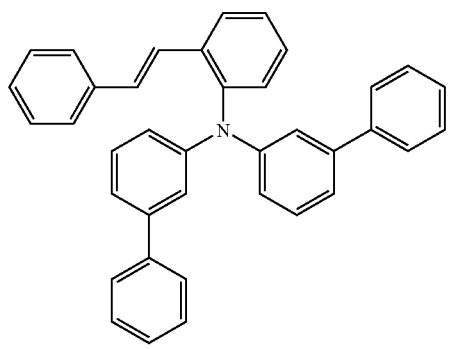

(57)
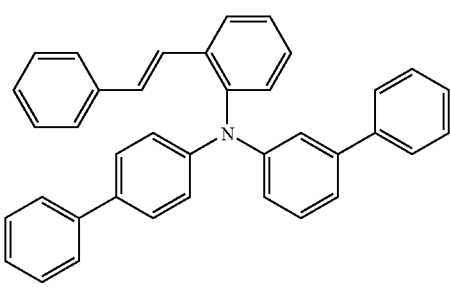

(58)
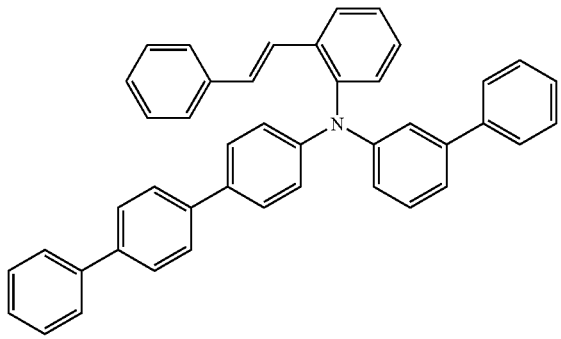

(59)
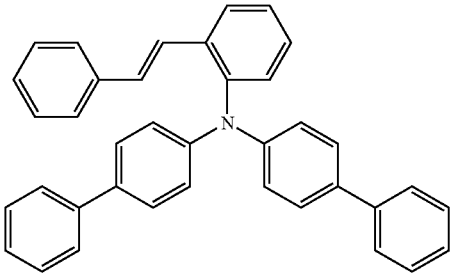

-continued

(60)
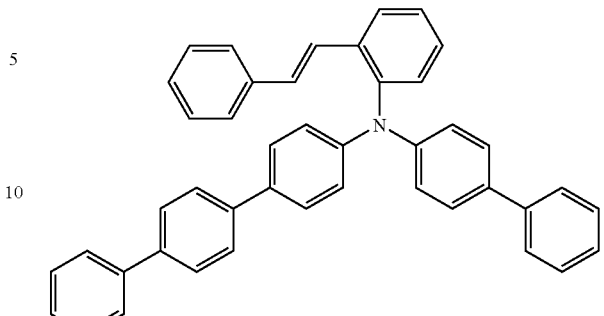

(61)
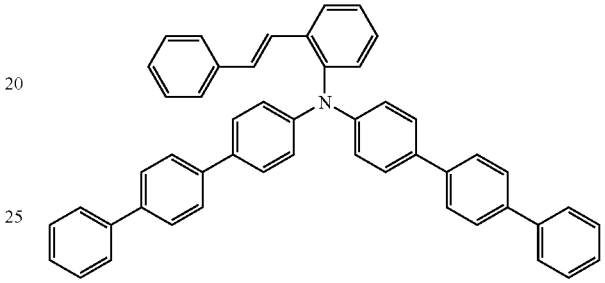

[Synthesis Method of the General Formula (1)]

Hereinafter, an example of a synthesis method for a stilbene derivative of the present invention, which is expressed by the following general formula (1) will be disclosed.

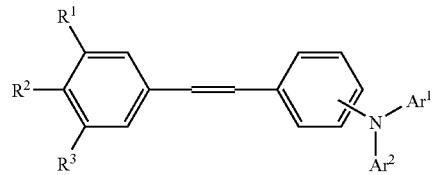
(1)

[Step 1: Synthesis of a Stilbene Derivative (St1) in Which One of 2-Position, 3-Position, and 4-Position is Halogenated]

First, as expressed by the following synthesis scheme (A), by reacting a benzaldehyde derivative (β1) with a benzyltriphenylphosphonium salt (α1) in which one of 2-position, 3-position, and 4-position is halogenated, which is obtained by reacting benzyl halide and triphenylphosphine, in the presence of a base, so-called, Wittig reaction; thus, a stilbene derivative (St1) in which one of 2-position, 3-position, and 4-position is halogenated is obtained. The stilbene derivative (St1) can also be obtained by Horner-Emmons reaction in which phosphonate ester (α2) is used instead of the triphenylphosphonium salt (α1), as shown in a synthesis scheme (A'). As the base, inorganic bases such as potassium carbonate or sodium carbonate, organic bases such as metal alkoxide, or the like can be used. Note that phosphonate ester (α2) is obtained by reacting benzyl halide with phosphate ester. $X^1$ and $X^2$ represent halogen atoms in the synthesis scheme (A) and the synthesis scheme (A'). In particular, bromine or iodine is preferable. Further, $R^1$ to $R^3$ represents alkyl groups having 1 to 3 carbon atoms, and $R^4$ represents an alkyl group having 1 to 10 carbon atoms.

Further, a stilbene derivative (St1), In addition, the stilbene derivative (St1) can also be obtained as represented by the synthesis scheme (A″) by a Wittig reaction in which benzaldehyde (β2) in which one of 2-position, 3-position, and 4-position is halogenated is reacted in the presence of a base with benzyltriphenylphosphonium salt (α3) which is unsubstituted or in which at least one of 3-position, 4-position, and 5-position is replaced by an alkyl group, which is obtained by reacting a benzyl halide derivative with triphenylphosphine. Alternatively, as shown by a synthesis scheme (A‴), this can be obtained by Horner-Emmons reaction in which phosphonate ester (α4) is used instead of the triphenylphosphonium salt (α3). Note that phosphonate ester (α4) is obtained by reacting a benzyl halide with phosphate ester $X^1$ and $X^2$ represent halogen atoms in the synthesis scheme (A″) and the synthesis scheme (A‴). In particular, bromine or iodine is preferable, and more preferably, bromine is used for $X^2$. Further, $R^1$ to $R^3$ represents alkyl groups having 1 to 3 carbon atoms, and $R^4$ represents an alkyl group having 1 to 10 carbon atoms.

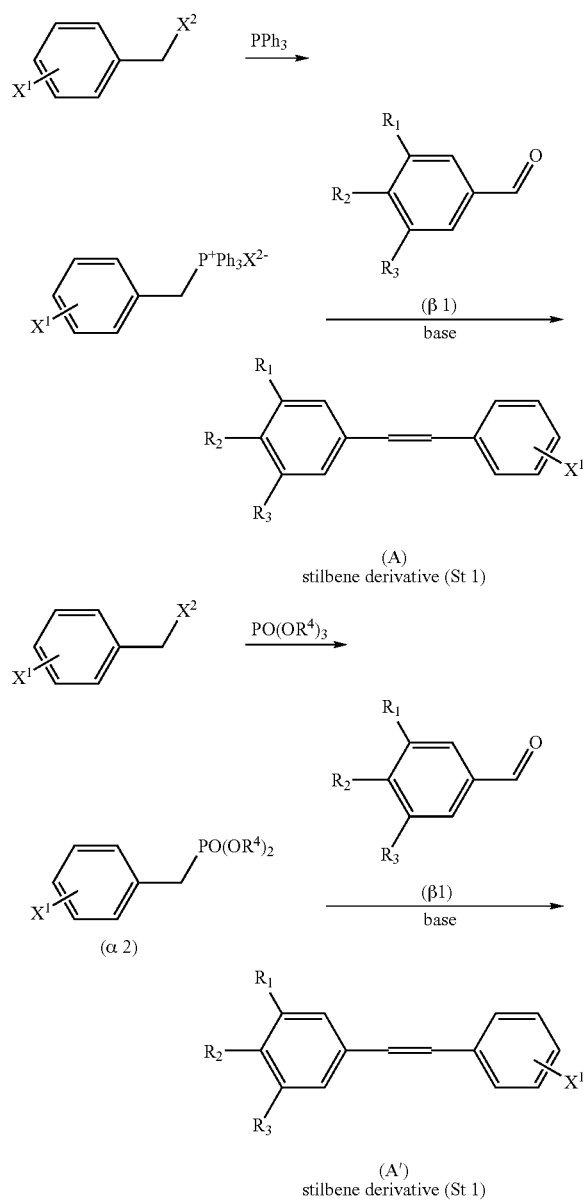

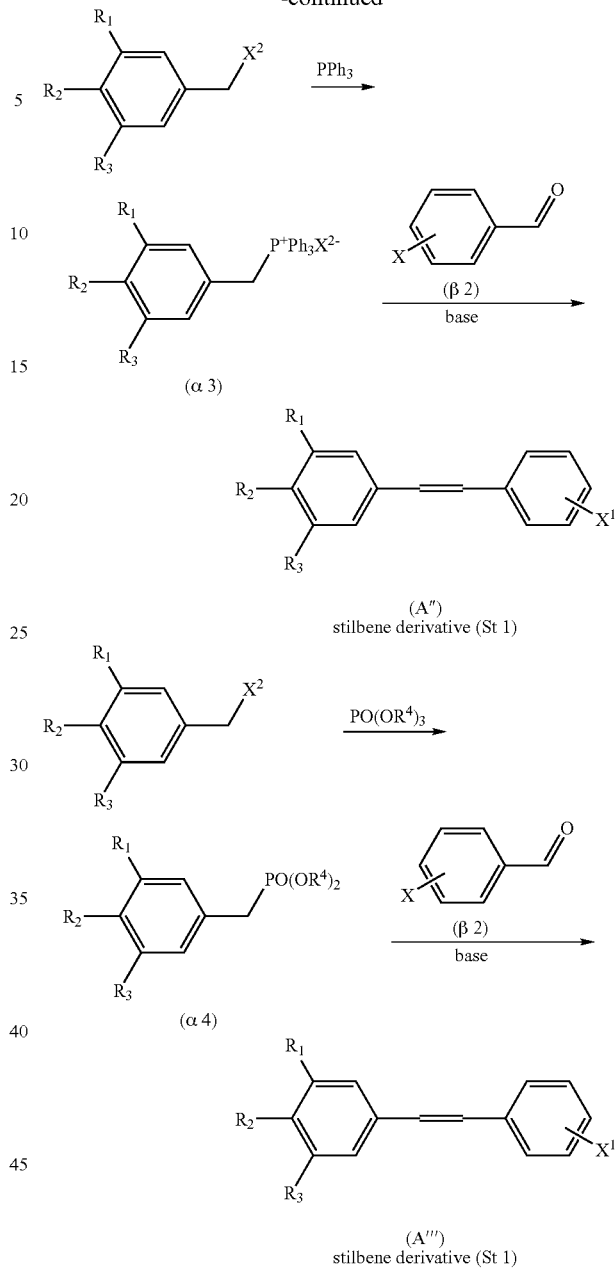

[Step 2: Synthesis of a Stilbene Derivative of the Present Invention, Which is Represented by the General Formula (1)]

Next, as shown by a synthesis scheme (B) below, a stilbene derivative (St1) obtained in Step 1 is coupled to arylamine ($Ar^1$—NH—$Ar^2$) in the presence of a base using a metal compound, a metal catalyst, or a metal; thus, a stilbene derivative of the present invention, which is represented by the general formula (1) can be obtained. As the metal catalyst in the coupling, a palladium catalyst such as palladium(II) acetate, tetrakis(triphenylphosphine)palladium (0), or bis(dibenzylideneacetone)palladium (0), or the like can be used. As the metal compound, monovalent copper typified by copper iodide or the like can be used, and copper or the like can be used as a metal. As the base, inorganic bases such as potassium carbonate or sodium carbonate, organic bases such as metal alkoxide, or the like can be used. $X^1$ represents a halogen atom in the synthesis scheme (B). In particular, bromine or iodine is preferable as the halogen.

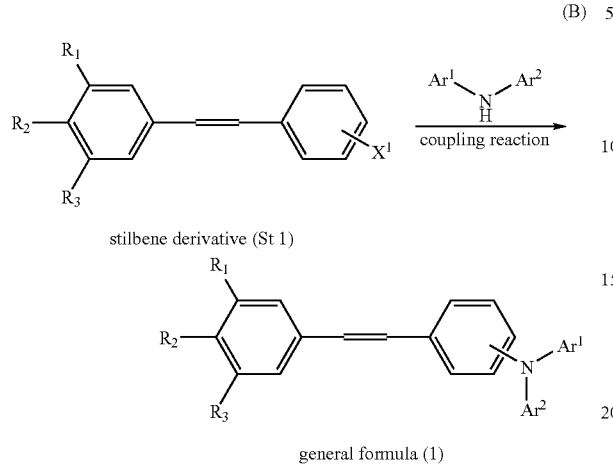

stilbene derivative (St 1)

general formula (1)

Note that arylamine (Ar$^1$—NH—Ar$^2$) in the above scheme can be synthesized by the following scheme, for example.

First, in the case where Ar$^1$ is a biphenyl group, halogen-substituted biphenyl of which 2-position, 3-position, or 4-position is replaced by halogen is coupled to 1 equivalent arylamine (Ar$^2$—NH$_2$) in the presence of a base by using a metal compound, a metal catalyst, or a metal as represented by a synthesis scheme (C-1); thus, desired arylamine (Ar$^1$—NH—Ar$^2$; Ar$^1$ is a biphenyl group) can be obtained. As the metal catalyst in the coupling, a palladium catalyst such as palladium(II) acetate, tetrakis(triphenylphosphine)palladium (0), or bis(dibenzylideneacetone)palladium(0), or the like can be used. As the metal compound, monovalent copper or the like can be used, and copper or the like can be used as a metal. As the base, inorganic bases such as potassium carbonate or sodium carbonate, organic bases such as metal alkoxide, or the like can be used. X$^3$ represents a halogen atom in the synthesis scheme (C-1). In particular, bromine or iodine is preferable. Note that in the synthesis scheme (C-1), the halogen substituted biphenyl may have a substituent, and as the substituent, an alkyl group having 1 to 4 carbon atoms can be given.

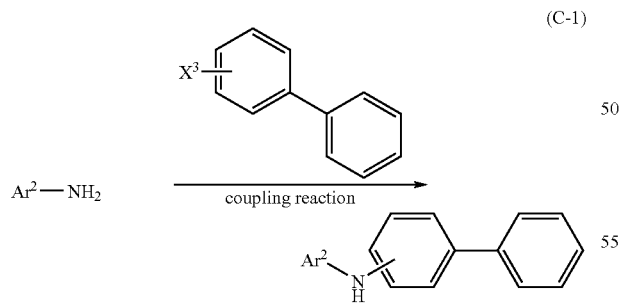

Further, in the case where both Ar$^1$ and Ar$^2$ are biphenyl groups, 2 equivalent phenylboronic acid is coupled with diphenylamine in which two phenyl groups are halogen-substituted in the presence of a base by using a metal catalyst, as presented by the following synthetic scheme (C-2); thus, desired arylamine (Ar$^1$—NH—Ar$^2$; both Ar$^1$ and Ar$^2$ are biphenyl groups) can be obtained. As a base, for example, an inorganic base such as potassium carbonate or sodium carbonate or an organic base such as metal alkoxide can be used. As the metal catalyst, a palladium catalyst such as palladium (II) acetate, tetrakis(triphenylphosphine)palladium(0), or bis (dibenzylideneacetone)palladium(0), can be used. This method has an advantage that N,N-di(4-biphenylyl)amine can be synthesized without using 4-aminobiphenyl which is a harmful substance to human body. X$^4$ and X$^5$ represent halogen atoms in a synthesis scheme (C-2). As the halogen, bromine or iodine is especially preferable.

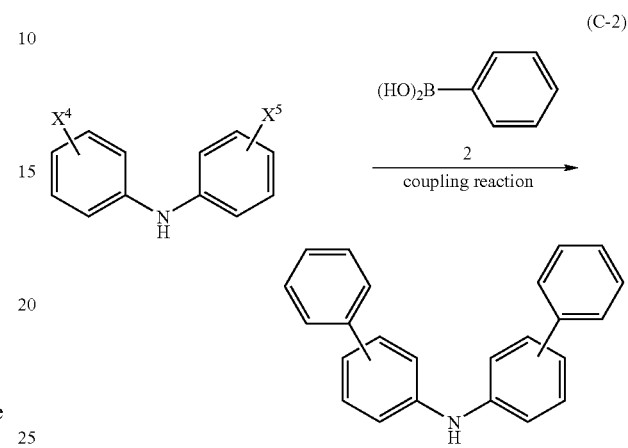

On the other hand, in the case where arylamine (Ar$^1$—NH—Ar$^2$) in which Ar$^1$ is a terphenyl group is synthesized, various terphenyl amines of which substituted positions are different can be synthesized by coupling 1 equivalent biphenylboronic acid of which the second position, the third position, or the fourth position is substituted by a boronic acid group with aniline of which the second position, the third position, or the fourth position is halogen-substituted in the presence of a base by using a metal catalyst, as represented by the following synthesis scheme (C-3). As the base, an inorganic base such as potassium carbonate or sodium carbonate, an organic base such as a metal alkoxide, or the like can be used. As the metal catalyst, a palladium catalyst such as palladium(II) acetate, tetrakis(triphenylphosphine)palladium (0), or bis(dibenzylideneacetone)palladium(0), or the like can be used. Then, as represented by the synthesis scheme (C-4), halogen-substituted (Ar$^2$—X) is coupled to the 1 equivalent terphenyl amine obtained as above in the presence of a base by using a metal compound, a metal catalyst, or a metal; thus, desired arylamine (Ar$^1$—NH—Ar$^2$; Ar$^1$ is a terphenyl group) can be obtained. As the metal catalyst in the coupling, a palladium catalyst such as palladium(II) acetate, tetrakis (triphenylphosphine)palladium(0), or bis(dibenzylideneacetone)palladium(0), or the like can be used. As the metal compound, monovalent copper or the like can be used, and copper or the like can be used as the metal. As the base, inorganic bases such as potassium carbonate or sodium carbonate, organic bases such as metal alkoxide, or the like can be used. X$^6$ to X$^9$ each represent a halogen atom in the synthesis scheme (C-3) and a synthesis scheme (C-4). In particular, bromine or iodine is preferable.

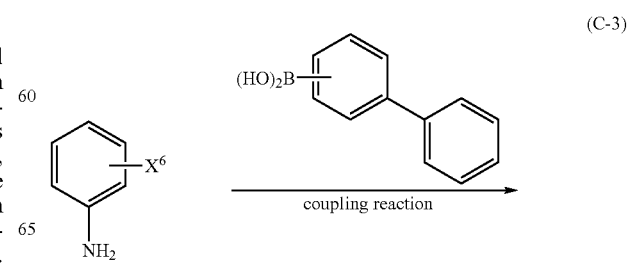

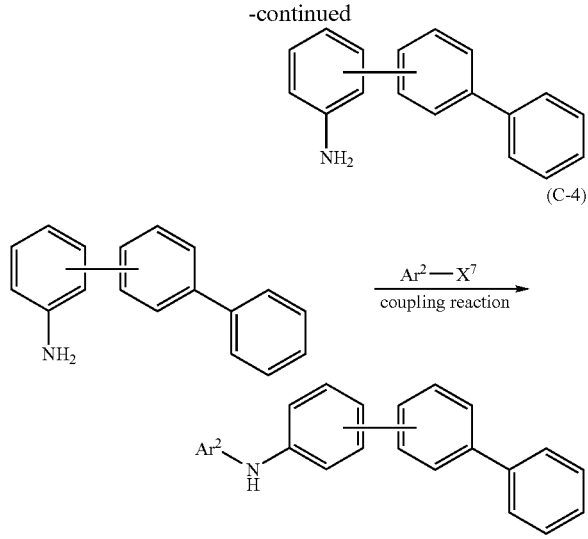

(C-4)

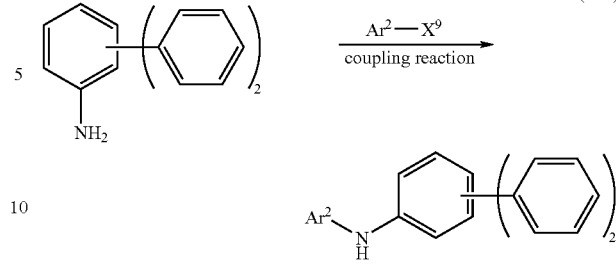

Further, in the Case where $Ar^1$ is a Terphenyl Group and a Center Benzene Ring of the terphenyl group is substituted by an amino group, aniline which is substituted by two halogen atoms is coupled with 2 equivalent phenylboronic acid by using a metal catalyst in the presence of a base as represented by the following synthetic scheme (C-5); thus, terphenyl amine is opinioned in which an amino group substitutes for a center benzene ring of the terphenyl group. As the base, an inorganic base such as potassium carbonate or sodium carbonate, an organic base such as a metal alkoxide, or the like can be used. As the metal catalyst, a palladium catalyst such as palladium(II) acetate, tetrakis(triphenylphosphine)palladium(0), or bis(dibenzylideneacetone)palladium(0), or the like can be used. Then, as represented by the synthesis scheme (C-6), halogen-substituted ($Ar^2$—X) is coupled to the obtained 1 equivalent terphenyl amine in the presence of a base by using a metal compound, a metal catalyst, or a metal; thus, desired arylamine ($Ar^1$—NH—$Ar^2$; $Ar^1$ is a terphenyl group) can be obtained. As the metal catalyst in the coupling, a palladium catalyst such as palladium(II) acetate, tetrakis (triphenylphosphine)palladium(0), or bis(dibenzylideneacetone)palladium(0), or the like can be used. As the metal compound, monovalent copper or the like can be used, and copper or the like can be used as the metal. As the base, inorganic bases such as potassium carbonate or sodium carbonate, organic bases such as metal alkoxide, or the like can be used.

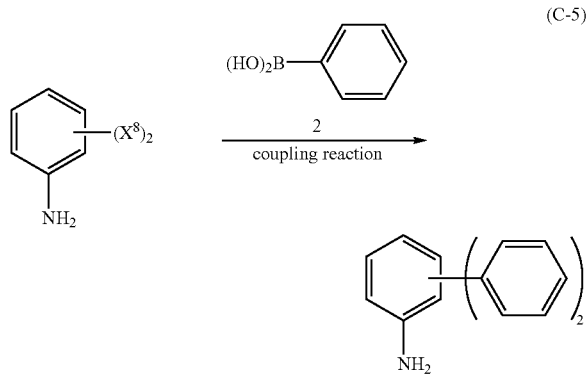

A stilbene derivative of the present invention has excellent heat resistance; therefore, by using the stilbene derivative of the invention for an electronics device, an electronics device which has excellent heat resistance can be obtained. Further, the stilbene derivative of the invention has good light emission efficiency; therefore, by using the stilbene derivative of the invention for an electronics device, a low consumption electronics device can be obtained.

Embodiment Mode 2

A mode of a light-emitting element using a stilbene derivative of the present invention will be hereinafter described with reference to FIG. 1A.

A light-emitting element of the present invention has a plurality of layers between a pair of electrodes. The plurality of layers are formed by stacking a layer containing a substance with a high carrier-injecting property and a layer containing a substance with a high carrier-transporting property so that a light-emitting region is formed apart from the electrodes, i.e., so that carrier recombination is carried out in a portion apart from the electrodes.

In this embodiment mode, the light-emitting element includes a first layer 103, a second layer 104, a third layer 105, and a fourth layer 106 which are sequentially stacked over a first electrode 102, and a second electrode 107 provided thereover. In the explanation of this embodiment mode, the first electrode 102 functions as an anode and the second electrode 107 functions as a cathode.

The substrate 101 is used as a support for the light-emitting element. As the substrate 101, for example, a glass substrate, a plastic substrate, or the like can be used. Other substrates than these can also be used as long as they can function as a support during a manufacturing process of the light-emitting element.

The first electrode 102 is preferably formed of a metal, alloy, conductive compound, mixture of these, or the like each having a high work function (specifically, 4.0 eV or higher). Specifically, as examples, indium tin oxide (ITO), indium tin oxide including silicon, indium zinc oxide (IZO) which is indium oxide contains zinc oxide (ZnO) at 2 to 20 wt %, indium oxide which contains tungsten oxide at 0.5 to 5 wt % and zinc oxide at 0.1 to 1 wt %, and the like are given. Films of these conductive metal oxides are usually formed by sputtering; however, a sol-gel method or the like may also be used. In addition, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), or the like is given.

The first layer 103 includes a substance with a high hole-injecting property and can be formed of molybdenum oxide, vanadium oxide, ruthenium oxide, tungsten oxide, manganese oxide, or the like. In addition, phthalocyanine (abbreviation: $H_2PC$), a phthalocyanine-based compound such as copper phthalocyanine (CuPC), a high-molecular weight material such as poly(ethylenedioxythiophene)/poly(styrenesulfonate) (PEDOT/PSS), or the like can also be used to form the first layer 103.

Moreover, the first layer 103 can be formed of a composite material including an organic compound and an inorganic compound. In particular, in a composite material including an organic compound and an inorganic compound exhibiting an electron-accepting property to the organic compound, electrons are transported between the organic compound and the inorganic compound to increase carrier density; thus, the hole-injecting property and the hole-transporting property are excellent.

When the first layer 103 is formed of a composite material including an organic compound and an inorganic compound, since ohmic contact with the first electrode 102 becomes possible, the material for the first electrode can be selected regardless of its work function.

The inorganic compound used for the composite material is preferably an oxide of a transition metal. Moreover, an oxide of a metal belonging to any of Groups 4 to 8 in the periodic table can be used. Specifically, vanadium oxide, niobium oxide, tantalum oxide, chromium oxide, molybdenum oxide, tungsten oxide, manganese oxide, and rhenium oxide are preferable since they have high electron-accepting properties. Above all, molybdenum oxide is preferable because it is stable in the air, it has a low moisture-absorption property, and it is easily handled.

The organic compound used for the composite material can be various kinds of compounds including an aromatic amine compound, a carbazole derivative, aromatic hydrocarbon, a high-molecular weight compound (such as polymer), and so on. The organic compound used for the composite material preferably has a high hole-transporting property. Specifically, a substance having a hole mobility of $10^{-6}$ cm$^2$/Vs or higher is preferable. However, other materials than those can also be used, as long as they have hole-transporting properties higher than electron-transporting properties. Specifically, the organic compound which can be used for the composite material will hereinafter be described below.

For example, the aromatic amine compound may be N,N'-di(p-tolyl)-N,N'-diphenyl-p-phenylenediamine (abbreviation: DTDPPA); 4,4'-bis[N-(4-diphenylaminophenyl)-N-phenylamino]biphenyl (abbreviation: DPAB); 4,4'-bis(N-{4-[N-(3-methylphenyl)-N-phenylamino]phenyl}-N-phenylamino)biphenyl (abbreviation: DNTPD); 1,3,5-tris[N-(4-diphenylaminophenyl)-N-phenylamino]benzene (abbreviation: DPA3B); or the like.

As the carbazole derivative which can be used for the composite material, specifically, the following can be given: 3-[N-(9-phenylcarbazol-3-yl)-N-phenylamino]-9-phenylcarbazole (abbreviation: PCzPCA1); 3,6-bis[N-(9-phenylcarbazol-3-yl)-N-phenylamino]-9-phenylcarbazole (abbreviation: PCzPCA2); 3-[N-(1-naphthyl)-N-(9-phenylcarbazol-3-yl)amino]-9-phenylcarbazole (abbreviation: PCzPCN1); or the like.

Moreover, 4,4'-di(N-carbazolyl)biphenyl (abbreviation: CBP); 1,3,5-tris[4-(N-carbazolyl)phenyl]benzene (abbreviation: TCPB); 9-[4-(N-carbazolyl)]phenyl-10-phenylanthracene (abbreviation: CzPA); 1,4-bis[4-(N-carbazolyl)phenyl-2,3,5,6-tetraphenylbenzene; or the like can be used.

As the aromatic hydrocarbon which can be used for the composite material, for example, the following can be given: 2-tert-butyl-9,10-di(2-naphthyl)anthracene (abbreviation: t-BuDNA); 2-tert-butyl-9,10-di(1-naphthyl)anthracene; 9,10-bis(3,5-diphenylphenyl)anthracene (abbreviation: DPPA); 2-tert-butyl-9,10-bis(4-phenylphenyl)anthracene (abbreviation: t-BuDBA); 9,10-di(2-naphthyl)anthracene (abbreviation: DNA); 9,10-diphenylanthracene (abbreviation: DPAnth); 2-tert-butylanthracene (abbreviation: t-BuAnth); 9,10-bis(4-methyl-1-naphthyl)anthracene (abbreviation: DMNA); 2-tert-butyl-9,10-bis[2-(1-naphthyl)phenyl]anthracene; 9,10-bis[2-(1-naphthyl)phenyl]anthracene; 2,3,6,7-tetramethyl-9,10-di(1-naphthyl)anthracene; 2,3,6,7-tetramethyl-9,10-di(2-naphthyl)anthracene; 9,9'-bianthryl; 10,10'-diphenyl-9,9'-bianthryl; 10,10'-bis(2-phenylphenyl)-9,9'-bianthryl; 10,10'-bis[(2,3,4,5,6-pentaphenyl)phenyl]-9,9'-bianthryl; anthracene; tetracene; rubrene; perylene; 2,5,8,11-tetra(tert-butyl)perylene; or the like. In addition to these, pentacene, coronene, or the like can also be used. In this way, the aromatic hydrocarbon having a hole mobility of $1 \times 10^{-6}$ cm$^2$ Vs or higher and 14 to 42 carbon atoms is more preferably used.

The aromatic hydrocarbon which can be used for the composite material may have a vinyl skeleton. As the aromatic hydrocarbon having a vinyl group, for example, 4,4'-bis(2,2-diphenylvinyl)biphenyl (abbreviation: DPVBi); 9,10-bis[4-(2,2-diphenylvinyl)phenyl]anthracene (abbreviation: DPVPA); or the like is given.

In addition, a high-molecular weight compound such as poly(N-vinylcarbazole) (abbreviation: PVK) or poly(4-vinyltriphenylamine) (abbreviation: PVTPA) can be used.

As a substance forming the second layer 104, a substance having a high hole-transporting property, specifically, an aromatic amine compound (that is, a compound having a benzene ring-nitrogen bond) is preferable. As a material that is widely used, 4,4'-bis[N-(3-methylphenyl)-N-phenylamino]biphenyl, derivatives thereof such as 4,4'-bis[N-(1-napthyl)-N-phenylamino]biphenyl (hereinafter referred to as NPB), and star burst aromatic amine compounds such as 4,4',4''-tris(N,N-diphenyl-amino)triphenylamine, and 4,4',4''-tris[N-(3-methylphenyl)-N-phenylamino]triphenylamine can be given. These materials described here mainly are substances each having a hole mobility of greater than or equal to $10^{-6}$ cm$^2$/Vs. However, other materials than these compounds may also be used as long as the hole transporting properties thereof are higher than the electron transporting properties. The second layer 104 is not limited to a single layer, and a mixed layer of the aforementioned substances, or a stacked layer which comprises two or more layers each including the aforementioned substance may be used.

The third layer 105 is a layer containing a substance with a light-emitting property (also referred to as a light-emitting substance). In this embodiment mode, the third layer 105 includes a stilbene derivative of the present invention described in Embodiment Mode 1. A stilbene derivative of the present invention exhibits light emission of blue to blue green, and thus, it can be preferably used as a light-emitting substance for a light-emitting element.

The fourth layer 106 can be formed of a substance with a high electron-transporting property. For example, the fourth layer 106 includes the following metal complex having a quinoline skeleton or a benzoquinoline skeleton, or the like: tris(8-quinolinolato)aluminum (abbreviation: Alq); tris(4-methyl-8-quinolinolato)aluminum (abbreviation: Almq$_3$); bis(10-hydroxybenzo[h]-quinolinato)beryllium (abbreviation: BeBq$_2$); bis(2-methyl-8-quinolinolato)-4-phenylphenolato-aluminum (abbreviation: BAlq); and the like. Besides those, the following metal complexes having an oxazole-based ligand or a thiazole-based ligand, or the like can be used: bis[2-(2-hydroxyphenyl)benzoxazolato]zinc (abbreviation: Zn(BOX)$_2$); bis[2-(2-hydroxyphenyl)benzothiazolato]zinc (abbreviation: Zn(BTZ)$_2$); and the like. Furthermore, in addition to the metal complexes, 2-(4-biphenylyl)-

5-(4-tert-butylphenyl)-1,3,4-oxadiazole (abbreviation: PBD); 1,3-bis[5-(p-tert-butylphenyl)-1,3,4-oxadiazol-2-yl] benzene (abbreviation: OXD-7); 3-(4-tert-butylphenyl)-4-phenyl-5-(4-biphenylyl)-1,2,4-triazole (abbreviation: TAZ); 3-(4-tert-butylphenyl)-4-(4-ethylphenyl)-5-(4-biphenylyl)-1,2,4-triazole (abbreviation: p-EtTAZ); bathophenanthroline (abbreviation: BPhen); bathocuproine (abbreviation: BCP); and the like can also be used. The substances mentioned here mainly have an electron mobility of $10^{-6}$ cm$^2$/Vs or higher. It is to be noted that the fourth layer 106 may include a substance other than those above as long as the substance has a higher electron-transporting property than hole-transporting property. Moreover, the fourth layer 106 may have not only a single-layer structure but also a stacked-layer structure including two or more layers formed of the above-mentioned substances.

The second electrode 107 can be formed of a metal, alloy, electrically conductive compound, or mixture of these, each having a low work function (specifically, 3.8 eV or lower). As a typical example of a cathode material, an element belonging to Group 1 or 2 in the periodic table, i.e., an alkali metal such as lithium (Li) or cesium (Cs), or an alkaline-earth metal such as magnesium (Mg), calcium (Ca), or strontium (Sr); an alloy containing any of these (such as MgAg or AlLi); a rare earth metal such as europium (Er) or ytterbium (Yb); an alloy containing a rare earth metal; or the like can be used. However, when a layer having a function of promoting electron injection is provided between the second electrode 107 and the light-emitting layer as a stack with the second electrode, the second electrode 107 can be formed of any of various conductive materials such as Al, Ag, ITO, or ITO including silicon regardless of its work function.

For the layer having a function of promoting electron injection, a compound of an alkali metal or an alkaline-earth metal, such as lithium fluoride (LiF), cesium fluoride (CsF), or calcium fluoride (CaF$_2$) can be used. Further, a layer including an electron-transporting substance which contains an alkali metal, an alkaline-earth metal, an alkali metal compound, or an alkaline-earth metal compound, for example, Alq mixed with lithium oxide and magnesium nitride, magnesium (Mg), or lithium (Li) may be used.

The first layer 103, the second layer 104, the third layer 105, and the fourth layer 106 can be formed by not only an evaporation method but also various methods such as an ink jet method or a spin coating method. Moreover, a different film-formation method may be used for each electrode or each layer.

In the light-emitting element of the present invention having the aforementioned structure, current flows by a potential difference generated between the first electrode 102 and the second electrode 107 and holes and electrons are recombined in the third layer 105, which is the layer containing a substance with a high light-emitting property; thus, light is emitted. In other words, in this structure, a light-emitting region is formed in the third layer 105.

Figure 1B:
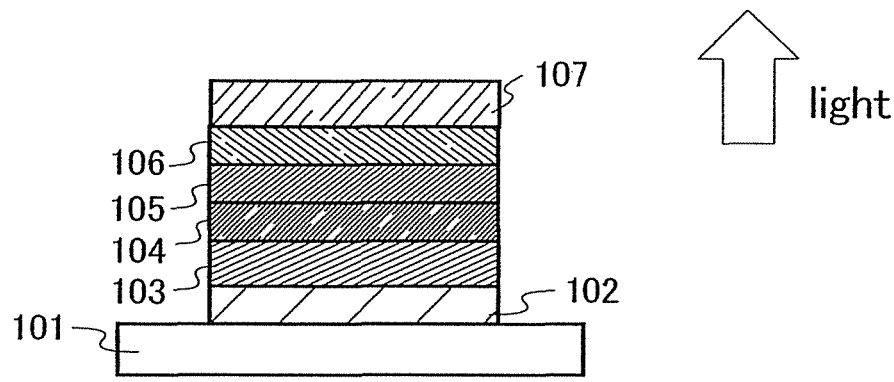
Figure 1C:
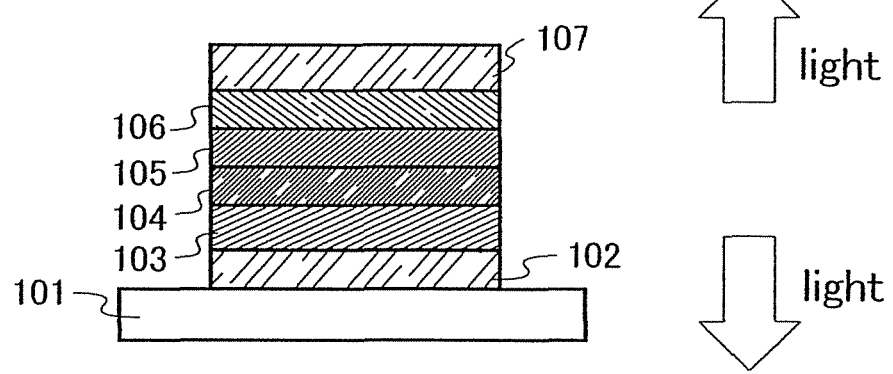

The emitted light is extracted to the outside through one or both of the first electrode 102 and the second electrode 107. Therefore, one or both of the first electrode 102 and the second electrode 107 is/are formed of a light-transmitting material. When only the first electrode 102 is formed of a light-transmitting material, the emitted light is extracted from the substrate side through the first electrode 102 as shown in FIG. 1A. Meanwhile, when only the second electrode 107 is an electrode formed of a light-transmitting material, the emitted light is extracted from the side opposite to the substrate side through the second electrode 107 as shown in FIG. 1B. When each of the first electrode 102 and the second electrode 107 is formed of a light-transmitting material, the emitted light is extracted from both the substrate side and the side opposite to the substrate side through the first electrode 102 and the second electrode 107 as shown in FIG. 1C.

The structure of the layers provided between the first electrode 102 and the second electrode 107 is not limited to the aforementioned one. A structure other than the aforementioned one may also be used as long as a light-emitting region in which holes and electrons are recombined is provided in a portion apart from the first electrode 102 and the second electrode 107 so that light extinction caused by approximation of the light-emitting region to metal is suppressed.

That is to say, the stacked-layer structure is not particularly limited, and layers containing a substance with a high electron-transporting property, a substance with a high hole-transporting property, a substance with a high electron-injecting property, a substance with a high hole-injecting property, a substance with a bipolar property (a material with a high electron and hole transporting property), a substance with a hole-blocking property, and the like may be freely combined with a stilbene derivative of the present invention.

Figure 2:
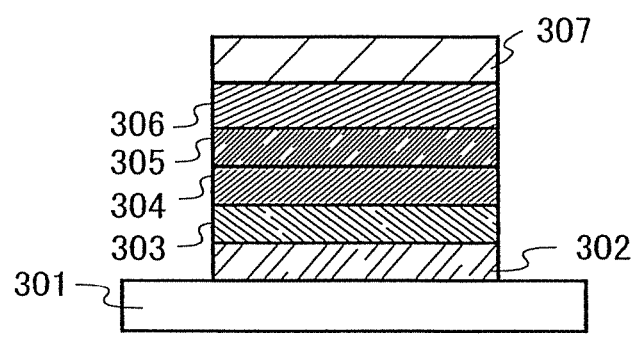
FIG. 2 illustrates a light-emitting element of the present invention.

A light emitting element shown in FIG. 2 has a structure in which a first layer 303 formed of a high electron transporting substance, a second layer 304 including a light-emitting substance, a third layer 305 formed of a high hole-transporting substance, a fourth layer 306 formed of a high hole-injecting property, and a second electrode 307 functioning as an anode are sequentially stacked over a first electrode 302 functioning as a cathode. It is to be noted that reference numeral 301 denotes a substrate.

In this embodiment mode, the light-emitting element is manufactured over a substrate made of glass, plastic, or the like. When a plurality of such light-emitting elements are manufactured over one substrate, a passive matrix type light-emitting device can be manufactured. Moreover, for example, thin film transistors (TFTs) may be formed over a substrate made of glass, plastic, or the like so that light-emitting elements are manufactured over electrodes electrically connected to the TFTs. Thus, an active matrix light-emitting device in which driving of the light-emitting elements is controlled by the TFTs can be manufactured. The structure of such TFTs is not particularly limited. The TFTs may be either a staggered type or an inverted staggered type. The crystallinity of a semiconductor used for the TFTs is not limited in particular, and the semiconductor may be either amorphous or crystalline. Moreover, a driver circuit formed on the TFT array substrate may include N-type and P-type TFTs or only one of N-type and P type TFTs.

Since a stilbene derivative of the present invention has a light-emitting property, it can be used as a light-emitting layer by itself as shown in this embodiment mode, without containing another light-emitting substance.

In addition, a film having an amorphous state using a stilbene derivative of the present invention can be obtained, because microcrystal components in forming the film is very scarce, and microcrystal components in the formed film is scarce. In other words, an excellent film quality can be obtained, and thus a favorable light-emitting element having almost no defects such as dielectric breakdown due to electric field concentration can be manufactured.

Furthermore, since a stilbene derivative of the present invention has excellent heat resistance, a light-emitting element having excellent heat resistance can be formed using the stilbene derivative of the present invention.

Moreover, since a stilbene derivative of the present invention has good light emission efficiency, when it is used in a light emitting element, a low power consumption light emitting element can be obtained.

Embodiment Mode 3

Embodiment Mode 3 will explain a light-emitting element with a structure different from the structure shown in Embodiment Mode 2.

The third layer 105 described in Embodiment Mode 2 includes a stilbene derivative of the present invention which is dispersed in another substance, so that the stilbene derivative of the present invention can emit light. The stilbene derivative of the present invention emits light of blue to blue green, and thus, a light-emitting element emitting light of blue to blue green can be provided.

As the substance in which a stilbene derivative of the present invention is dispersed, various materials such as the following can be used. For example, 9-[4-(N-carbazolyl)phenyl]-10-phenylanthracene (abbreviation: CzPA)-4,4'-di(N-carbazolyl)biphenyl (abbreviation: CBP), 2,2',2''-(1,3,5-benzenetriyl)tris(1-phenyl-1H-benzimidazole) (abbreviation: TPBI), 4,4',4''-tri(N-carbazolyl)triphenylamine (abbreviation: TCTA), 9,10-di(2-naphthyl)anthracene (abbreviation: DNA), 2-tert-butyl-9,10-di(2-naphthyl)anthracene (abbreviation: t-BuDNA), and the like can be used.

Since the stilbene derivative of the present invention has high heat resistance, a light-emitting element with the use of the stilbene derivative of the present invention can have excellent heat resistance.

Further, since a stilbene derivative of the present invention has good light emission efficiency, when it is used in a light emitting element, a low power consumption light emitting element can be obtained.

The structures described in Embodiment Mode 2 can be applied to the other elements than the third layer 105.

Embodiment Mode 4

This embodiment mode will explain a light-emitting device manufactured by using a stilbene derivative of the present invention.

Figure 3A:
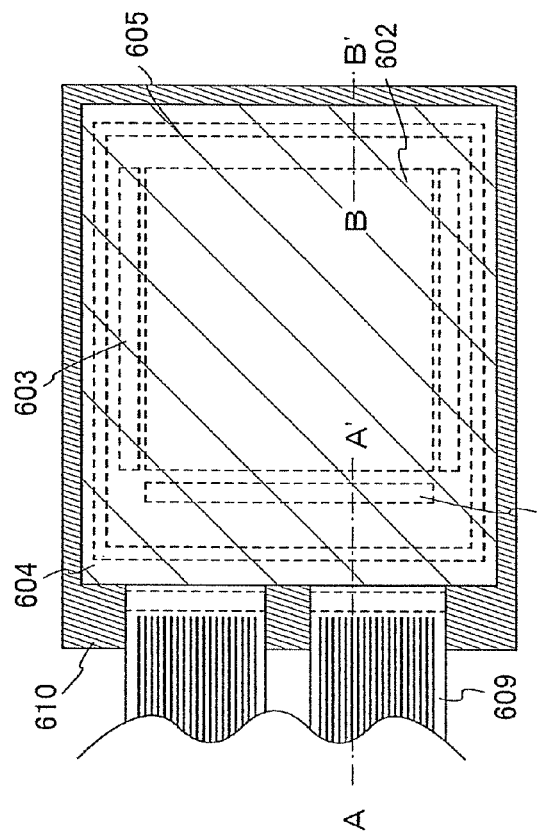
FIGS. 3A and 3B illustrate a light-emitting device of the present invention.
Figure 3B:
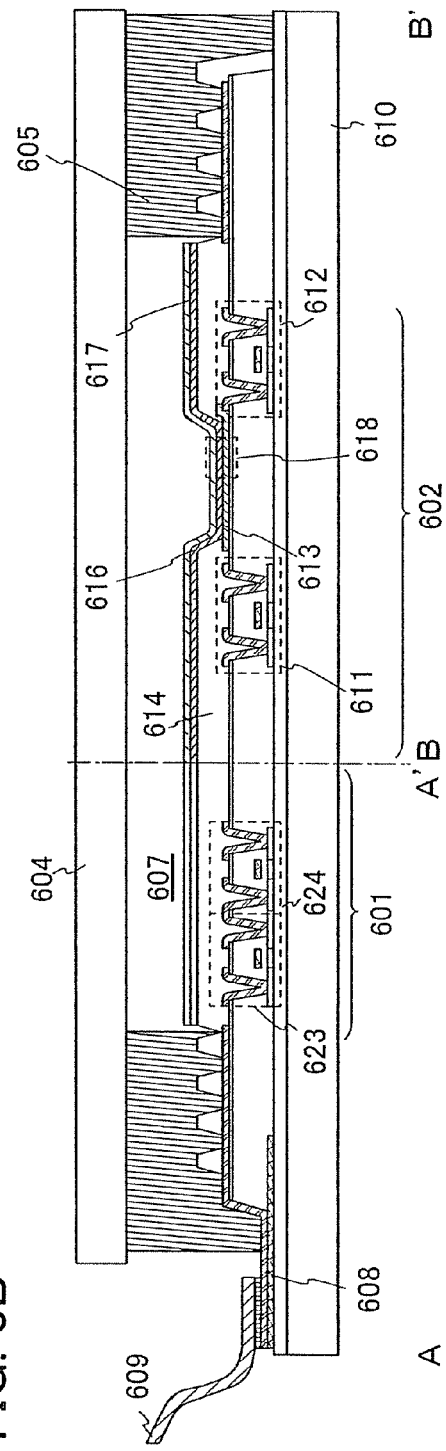

In this embodiment mode, a light-emitting device manufactured by using a stilbene derivative of the present invention is explained with reference to FIGS. 3A and 3B. FIG. 3A is a top view of the light-emitting device, while FIG. 3B is a cross-sectional view along a line A-A' and a line B-B' in FIG. 3A. This light-emitting device includes a driver circuit portion (source side driver circuit) 601, a pixel portion 602, and a driver circuit portion (gate side driver circuit) 603 in order to control the light emission of the light-emitting element. Moreover, reference numeral 604 denotes a sealing substrate; 605, a sealant; and 607, a space surrounded by the sealant 605.

A lead wiring 608 transmits signals to be inputted to the source side driver circuit 601 and the gate side driver circuit 603 and receive a video signal, a clock signal, a start signal, a reset signal, and the like from an FPC (Flexible Printed Circuit) 609 which is an external input terminal. Although only an FPC is shown here, this FPC may have a printed wiring board (PWB) attached. In this specification, the light-emitting device includes not only a light-emitting device alone but also a light-emitting device with an FPC or a PWB attached thereto.

Next, the cross-sectional structure is explained with reference to FIG. 3B. Although the driver circuit portion and the pixel portion are formed over an element substrate 610, the source side driver circuit 601 as the driver circuit portion and one pixel in the pixel portion 602 are shown here.

In the source side driver circuit 601, a CMOS circuit in which an n-channel TFT 623 and a p-channel TFT 624 are combined is formed. The driver circuit may be formed by various CMOS circuits, PMOS circuits, or NMOS circuits. Although this embodiment mode describes a driver-integrated type in which the driver circuit is formed over the substrate, the structure may be different. For example, the driver circuit may be formed not over the substrate but outside the substrate. Further, the crystallinity of a semiconductor used for TFTs is not limited either, and either an amorphous semiconductor or a crystalline semiconductor can be used.

Moreover, the pixel portion 602 is formed with a plurality of pixels including a switching TFT 611, a current controlling TFT 612, and a first electrode 613 electrically connected to a drain of the current controlling TFT 612. An insulator 614 is formed covering an end portion of the first electrode 613. Here, the insulator 614 is formed using a positive photosensitive acrylic resin film.

In order to have favorable coverage, the insulator 614 is formed so as to have a curved surface with curvature at its upper end or lower end portion. For example, in a case of using a positive photosensitive acrylic for the insulator 614, only the upper end portion of the insulator 614 preferably has a curved surface with a radius of curvature (0.2 to 3 μm). As the insulator 614, either a negative type which becomes insoluble in etchant by light irradiation or a positive type which becomes soluble in etchant by light irradiation can be used.

An EL layer 616 and a second electrode 617 are formed over the first electrode 613. Here, the first electrode 613 functioning as an anode is preferably formed of a material with a high work function. For example, a single-layer film of an ITO film, an indium tin oxide film including silicon, an indium oxide film containing 2 to 20 wt % of zinc oxide, a titanium nitride film, a chromium film, a tungsten film, a Zn film, a Pt film, or the like can be used. Besides these single-layer films, a stack of a titanium nitride film and a film containing aluminum as its main component, a stack of three layers of a titanium nitride film, a film containing aluminum as its main component, and a titanium nitride film, or the like can be used. When a stacked-layer structure is employed, the first electrode 613 can have low resistance as wiring, obtain favorable ohmic contact, and moreover function as an anode.

The EL layer 616 is formed by various methods such as an evaporation method using an evaporation mask, an inkjet method, or a spin coating method. The EL layer 616 includes a stilbene derivative of the present invention shown in Embodiment Mode 1. As another material for forming the EL layer 616, a low molecular weight material, an intermediate molecular weight material which has properties between those of a high molecular weight material and a low molecular weight material (such as oligomer and dendrimer), or a high molecular weight material may be used. In addition, a single layer or a stack of organic compound(s) is generally used as a material of an EL layer; however, in the present invention, a structure in which an organic compound is used in a film formed of an organic compound can be used.

The second electrode 617 which is formed over the EL layer 616 and functions as a cathode is preferably formed of a material with a low work function (Al, Mg, Li, Ca, or an alloy or compound thereof, e.g., MgAg, MgIn, AlLi, LiF, or $CaF_2$). When light generated in the EL layer 616 passes through the second electrode 617, the second electrode 617 is preferably formed from a stack of a thin metal film and a transparent conductive film (ITO, indium oxide including 2 wt % to 20 wt % of zinc oxide, an indium tin oxide containing silicon, zinc oxide (ZnO), or the like).

When the sealing substrate 604 and the element substrate 610 are attached to each other with the sealant 605, a light-emitting element 618 is provided in the space 607 surrounded by the element substrate 610, the sealing substrate 604, and the sealant 605. The space 607 is filled with a filler, which may be an inert gas (such as nitrogen or argon) or the sealant 605.

The sealant 605 is preferably formed of an epoxy-based resin. It is desirable that the material of the sealant 605 preferably allows as little moisture and oxygen as possible to penetrate. As the sealing substrate 604, a plastic substrate formed of FRP (Fiberglass-Reinforced Plastics), PVF (polyvinyl fluoride), polyester, acrylic, or the like can be used, in addition to a glass substrate or a quartz substrate.

As described above, the light-emitting device manufactured by the stilbene derivative of the present invention can be obtained.

The light-emitting device of the present invention uses the aromatic amine compound shown in Embodiment Mode 1; therefore, the light-emitting device can have favorable characteristics. Specifically, the light-emitting device can have high heat resistance.

Further, since a stilbene derivative of the present invention has good light emission efficiency, a low power consumption light emitting device can be obtained.

Figure 4A:
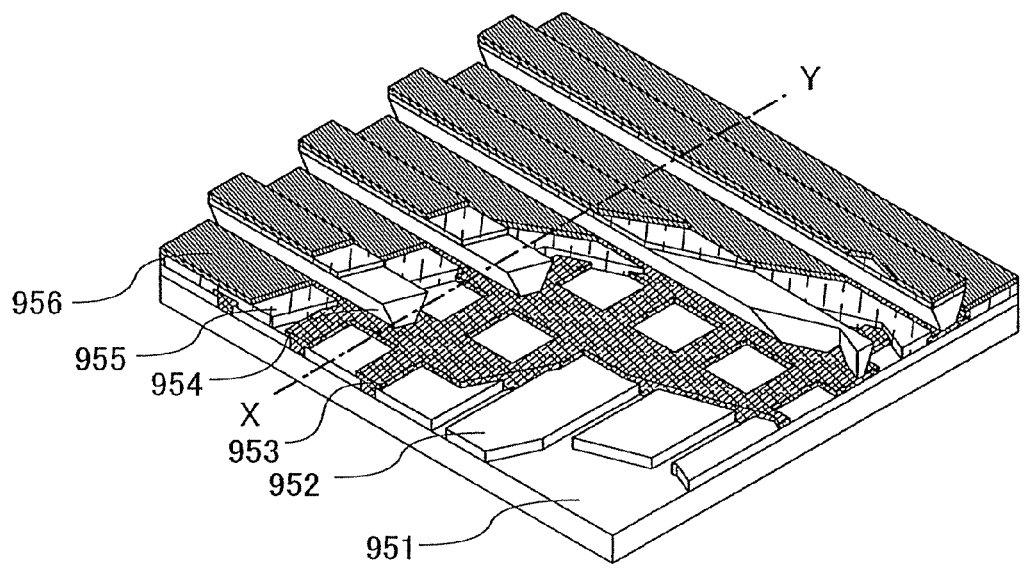
FIGS. 4A and 4B illustrate a light-emitting device of the present invention.
Figure 4B:
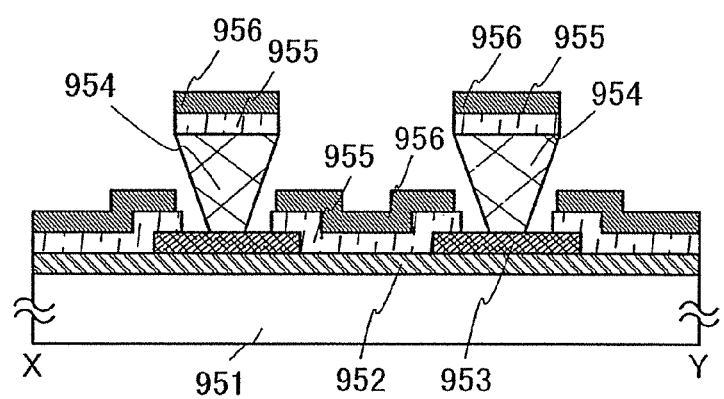

This embodiment mode has described the active matrix type light-emitting device in which the driving of the light-emitting element is controlled by a transistor. However, a passive matrix type light-emitting device may be adopted instead. FIG. 4A is a perspective view of a passive matrix type light-emitting device manufactured by applying the present invention. In FIGS. 4A and 4B, an EL layer 955 is provided over a substrate 951 and between an electrode 952 and an electrode 956. End portions of the electrode 952 are covered with an insulating layer 953. Then, a partition layer 954 is provided over the insulating layer 953. A side wall of the partition layer 954 slopes so that a distance between one side wall and the other side wall becomes narrow toward a substrate surface. In other words, a cross section of the partition layer 954 in the direction of a narrow side is trapezoidal, and a base (a side facing in a similar direction to a plane direction of the insulating layer 953 and being in contact with the insulating layer 953) is shorter than an upper side (a side facing in a similar direction to the plane direction of the insulating layer 953 and not being in contact with the insulating layer 953). A defect of the light-emitting element due to static electricity or the like can be prevented by providing the partition layer 954 in this manner. In addition, the passive matrix type light-emitting device can also have excellent heat resistance when it includes the light-emitting element of the present invention. Further, a low power consumption light emitting device can be obtained.

Embodiment Mode 5

This embodiment mode explains electronic devices of the present invention which includes the light-emitting device described in Embodiment Mode 4 as its component. The electronic devices of the present invention include stilbene derivatives of the present invention described in Embodiment Mode 1 and have display portions with high heat resistance. Further, each of the electronic devices has a display portion with reduced power consumption.

Examples of the electronic devices having the light-emitting elements manufactured using stilbene derivatives of the present invention include the following: cameras such as video cameras or digital cameras, goggle type displays, navigation systems, sound reproducing devices (car audio systems, audio components, or the like), computers, game machines, mobile information terminals (mobile computers, cellular phones, mobile game machines, electronic books, or the like), image reproducing devices having recording media (specifically, a device which reproduces content of a recording medium such as a digital versatile disc (DVD) and has a display device for displaying the image), and the like. Specific examples of these electronic devices are shown in FIGS. 5A to 5D.

Figure 5A:
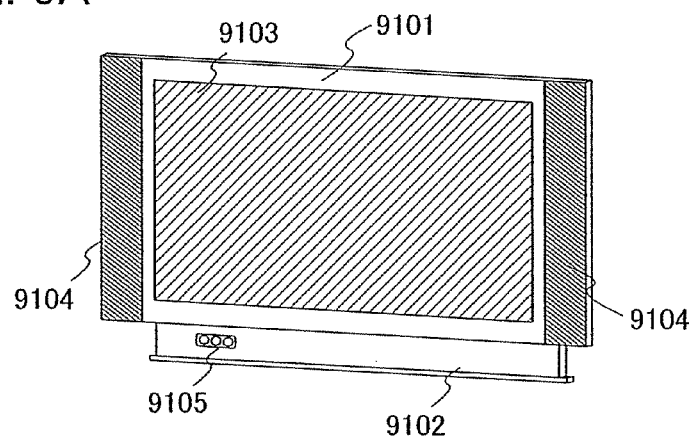
FIGS. 5A to 5D illustrate electronic devices of the present invention.

FIG. 5A illustrates a television device according to the present invention which includes a housing 9101, a support base 9102, a display portion 9103, speaker portions 9104, a video input terminal 9105, and the like. In this television device, the display portion 9103 includes light-emitting elements similar to those described in Embodiment Modes 2 to 4, which are arranged in matrix. The light-emitting element has a feature of high heat resistance. Further, it is another feature that the light emission efficiency is good. The display portion 9103 which includes the light-emitting element also has a similar feature, and thus the television device has high heat resistance and power consumption thereof is reduced.

Figure 5B:
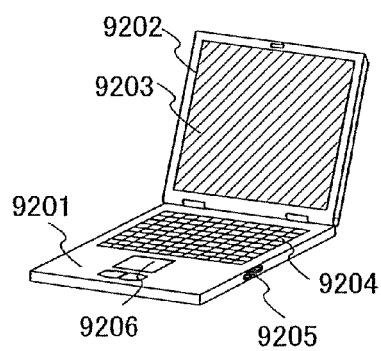

FIG. 5B illustrates a computer according to the present invention which includes a main body 9201, a housing 9202, a display portion 9203, a keyboard 9204, an external connection port 9205, a pointing device 9206, and the like. In this computer, the display portion 9203 includes light-emitting elements similar to those described in Embodiment Modes 2 to 4, which are arranged in matrix. The light-emitting element has a feature of high heat resistance. Further, it is another feature that the light emission efficiency is good. The display portion 9203 which includes the light-emitting element also has a similar feature, and thus the computer device has high heat resistance and power consumption thereof is reduced.

Figure 5C:
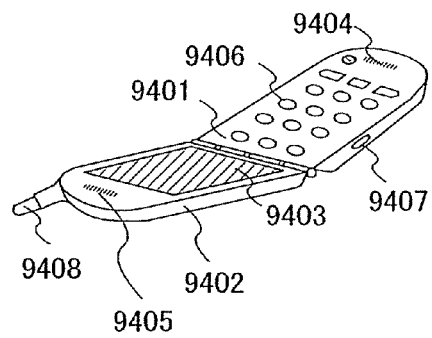

FIG. 5C illustrates a cellular phone according to the present invention which includes a main body 9401, a housing 9402, a display portion 9403, an audio input portion 9404, an audio output portion 9405, operation keys 9406, an external connection port 9407, an antenna 9408, and the like. In this cellular phone, the display portion 9403 includes light-emitting elements similar to those described in Embodiment Modes 2 to 4, which are arranged in matrix. The display portion 9403 which includes the light-emitting element also has a similar feature, and thus the cellular phone has high heat resistance and power consumption thereof is reduced.

Figure 5D:
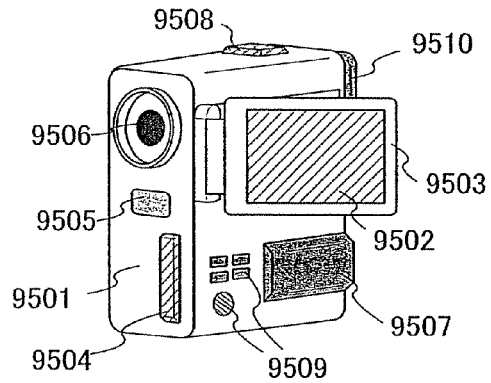

FIG. 5D illustrates a camera according to the present invention which includes a main body 9501, a display portion 9502, a housing 9503, an external connection port 9504, a remote control receiving portion 9505, an image receiving portion 9506, a battery 9507, an audio input portion 9508, an operation key 9509, an eye piece portion 9510, and the like. In this camera, the display portion 9502 includes light-emitting elements similar to those described in Embodiment Modes 2 to 4, which are arranged in matrix. The light-emitting element has a feature of high heat resistance. The display portion 9502 which includes the light-emitting element also has a similar feature, and thus the camera has high heat resistance and power consumption thereof is reduced.

As described above, the applicable range of the light-emitting device of the present invention is so wide that the light-emitting device can be applied to electronic devices in various fields. By the use of a stilbene derivative of the present invention, low power consumption electronic devices including display portions with high heat resistance can be provided.

In addition, the light-emitting device of the present invention can also be used as a lighting device. One mode of using the light-emitting element of the present invention as a lighting device is explained with reference to FIG. 6.

Figure 6:
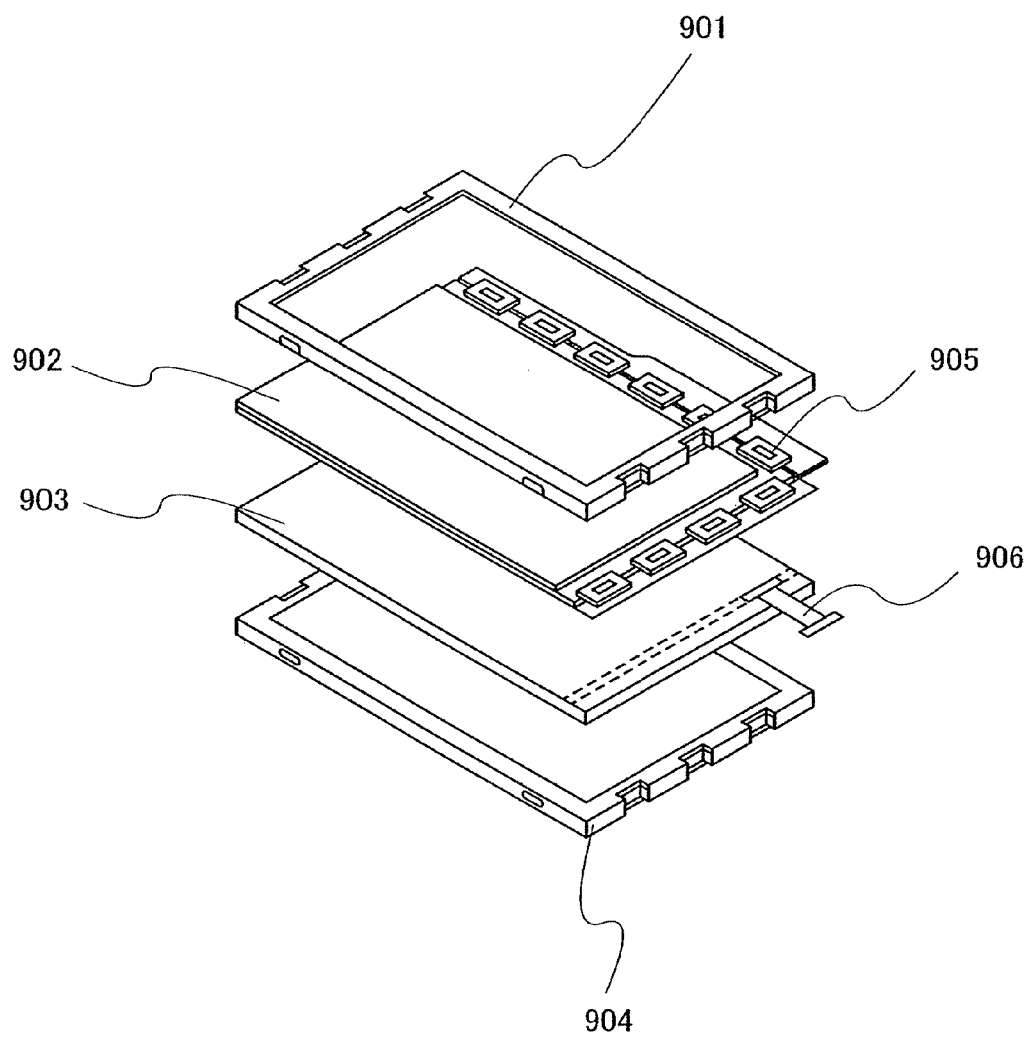
FIG. 6 illustrates an electronic device of the present invention.

FIG. 6 illustrates an example of a liquid crystal display device using the light-emitting device of the present invention as a backlight. The liquid crystal display device shown in FIG. 6 includes a housing 901, a liquid crystal layer 902, a backlight 903, and a housing 904. The liquid crystal layer 902 is connected to a driver IC 905. The light-emitting device of the present invention is used as the backlight 903, to which current is supplied through a terminal 906.

By using the light-emitting device of the present invention as a backlight of the liquid crystal display device, the backlight with reduced consumption can be obtained. Since the light-emitting device of the present invention is a surface light-emitting lighting device and can be formed to have a large area, a larger-area backlight can be obtained and a larger-area liquid crystal display device can also be obtained. A light emitting device of the invention is thin and consumes low power; thus, thinner display devices with reduced power consumption can be obtained. Further, since a light emitting device of the invention has excellent heat resistance, a liquid crystal display device using a light emitting device of the invention has also excellent heat resistance.

Example 1

In this example, a synthesis example of (E)-4-[N-(4-biphe-niryl)-N-phenylamino]stilbene (hereinafter referred to as BPAS), which is the stilbene derivative of the invention expressed by the following structural formula (9), will be described concretely.

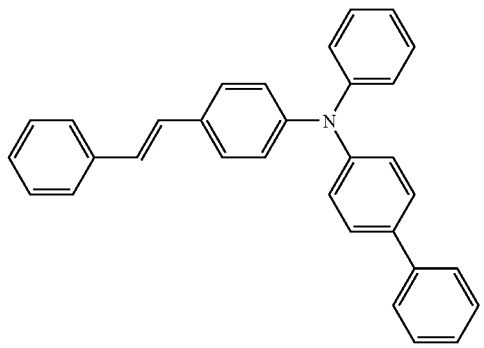

[Step 1]

Synthesis of 4-bromostilbene is described. A synthesis scheme of 4-bromostilbene is represented by (a-1) and (a-2).

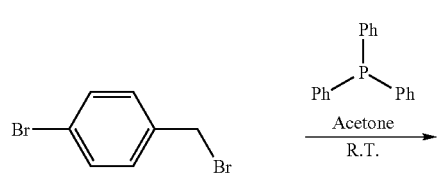

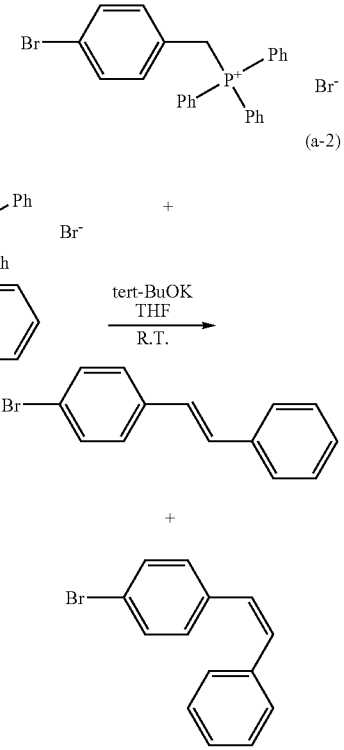

(i) A Synthetic Method of 4-Bromobenzyl Triphenylphosphonium Bromide

First, 25.2 g (101 mmol) of 4-bromobenzylbromide and 100 mL of acetone were put in a 200 mL conical flask, and 29.1 g (111 mmol) of triphenylphosphine was added thereto. The mixture was stirred for 23 hours at room temperature. After the reaction was finished, a precipitate in the reaction mixture was collected by suction filtration, and 50.5 g of a white powdered solid of 4-bromobenzyl triphenylphosphonium bromide that was a target substance was obtained in a yield of 98%.

(ii) Synthesis of 4-bromostilbene 25.3 g (49.5 mmol) of 4-bromobenzyl triphenylphosphonium bromide, which was obtained in (i), and 5.25 g (49.5 mmol) of benzaldehyde were put in a 500 mL three-neck flask, and nitrogen substitution was carried out in the flask. Then, 250 mL of dehydrated tetrahydrofuran (abbreviation: THF) was added to the mixture. Further, a suspension in which 6.10 g (54.4 mmol) of potassium tert-butoxide and 60 mL of dehydrated THF were mixed was dropped to the mixture. Subsequently, the mixture was stirred for 24 hours at room temperature. After the reaction was finished, the reaction solution was washed with water, and an aqueous layer was extracted with ethyl acetate, and the extraction solution was mixed with an organic layer and then dried with magnesium sulfate. After the drying, suction filtration of the mixture was carried out, and the filtrate was concentrated. The obtained residue was purified by silica gel column chromatography (eluent; toluene), and the obtained solution was concentrated. The obtained solid was washed with methanol. The solid in the methanol suspension was collected by suction filtration to obtain 3.75 g of white powdery solid of (E)-4-bromostilbene that was a target substance in a yield of 29%. Note that in the reaction, (Z)-4-bromostilbene was also observed; however, only (E)-4-bromostilbene was isolated and purified.

[Step 2]

A synthesis method of 4-phenyldiphenylamine will be described. A synthesis scheme of 4-phenyldiphenylamine is shown in (a-3).

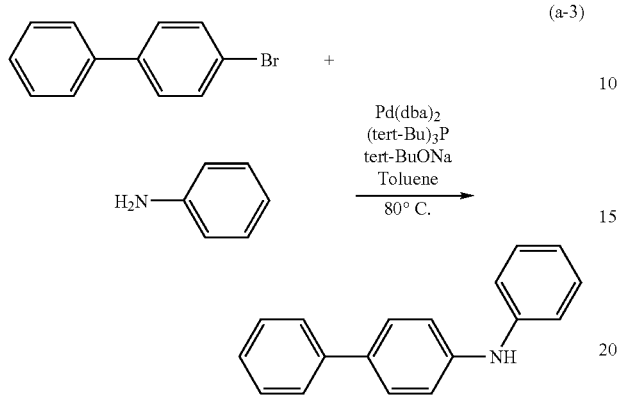

(a-3)

40.0 g (172 mmol) of 4-bromobiphenyl, 0.986 g (1.72 mmol) of bis(dibenzylideneacetone)palladium(0), and 41.2 g (429 mmol) of sodium-tert-butoxide (Abbreviation: tert-BuONa) were put in a 500 mL three-neck flask, and nitrogen substitution was carried out in the flask. 300 mL of toluene, 19.2 g (206 mmol) of aniline, and 5.90 g (2.92 mmol) of tri(tert-butyl) phosphine (10% hexane solution) were added to the mixture. The reaction mixture was stirred at 80° C. for 2 hours. After the reaction, the reaction mixture was washed with water, and an aqueous layer is extracted with ethyl acetate, and the extraction solution was combined with an organic layer dried and then dried with magnesium sulfate. After the drying, suction filtration of the mixture was carried out, and the filtrate was concentrated. The obtained residue was dissolved in toluene, and then was filtrated through Florisil, Celite, and alumina. The filtrate was concentrated, and an obtained solid was recrystallized using a mixed solvent of toluene and hexane; thus, 33.4 g of white color powdery solid of 4-phenyldiphenylamine was obtained in a yield of 79%.

[Step 3]

A synthesis method of BPAS will be described. A synthesis scheme of BPAS is represented by (a-4).

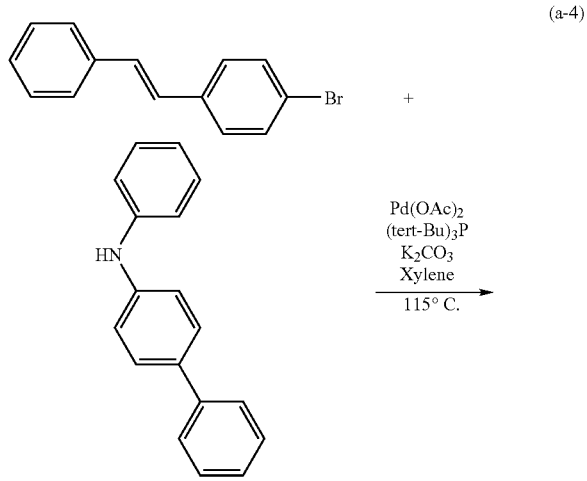

(a-4)

0.93 g (3.6 mmol) of (E)-4-bromostilbene, 0.88 g (3.6 mmol) of 4-phenyl diphenylamine, 0.0081 g (0.036 mmol) of palladium(II) acetate, and potassium carbonate 1.5 g (11 mmol) were put into a 100 mL three-necked flask, and the inside was substituted by nitrogen. 50 mL of xylene and 0.22 g (0.11 mmol) of tri(tert-butyl)phosphine (10% hexane solution) were added to the mixture. The reaction mixture was stirred at 115° C. for 17 hours. After the reaction was finished, the reaction solution was washed with water, and an aqueous layer was extracted with ethyl acetate, and the extraction solution was mixed with an organic layer and then dried with magnesium sulfate. After the drying, suction filtration of the mixture was carried out, and the filtrate was concentrated. The obtained residue was purified by silica gel column chromatography (eluent; toluene), and the obtained solution was concentrated. The obtained solid was recombined with a mixed solvent of chloroform and hexane to be recrystallized and 3.2 g of an objective matter, a lemon-yellow powder solid of BPAS that was a target substance was obtained in a yield of 48%.

The thermogravimetry-differential thermal analysis (TG-DTA) of BPAS was performed using a thermo-gravimetric/differential thermal analyzer (TG/DTA 320, product of Seiko Instruments Inc.). The thermophysical properties were evaluated under a nitrogen atmosphere at a rate of temperature rise of 10° C./min. As a result, based on the relationship between gravity and temperature (thermogravimetric measurement), the temperature under normal pressure was 323° C., which is the temperature at which the gravity is 95% or less of the gravity at the starting point of the measurement. It was found that BPAS had good heat resistance.

Figure 7:
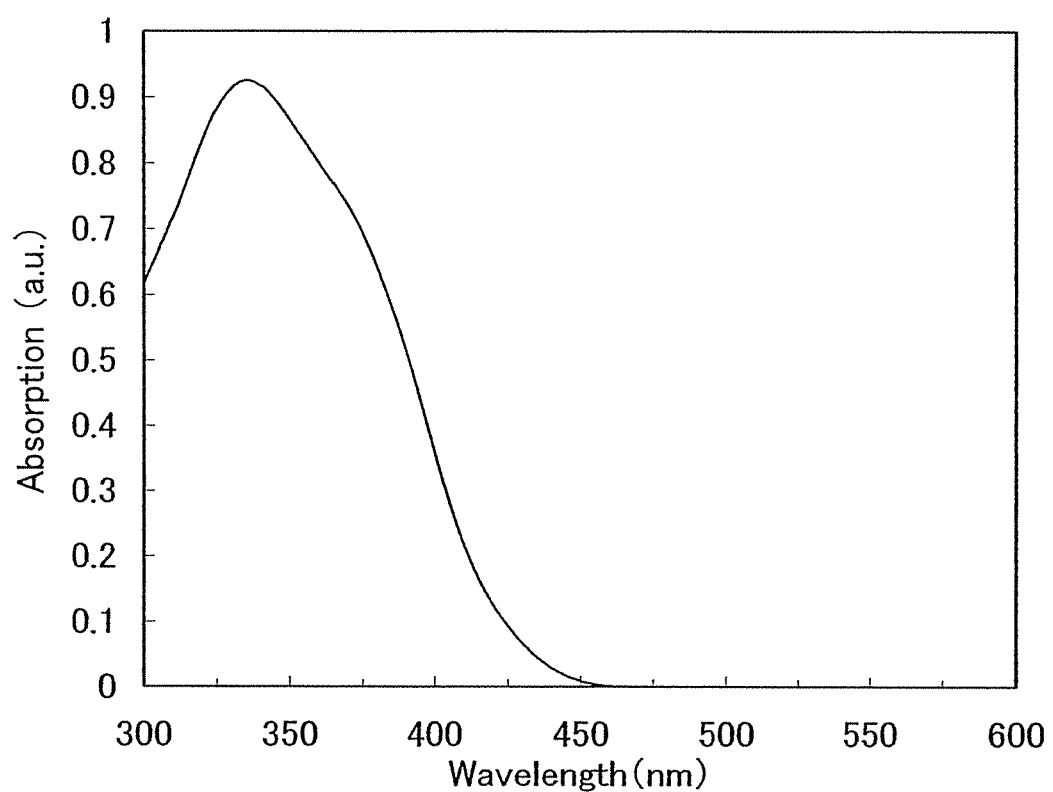
FIG. 7 is a graph showing an absorption spectrum in a toluene solution of 4-[N-(4-biphenylyl)-N-phenylamino]stilbene which is a stilbene derivative of the present invention.
Figure 8:
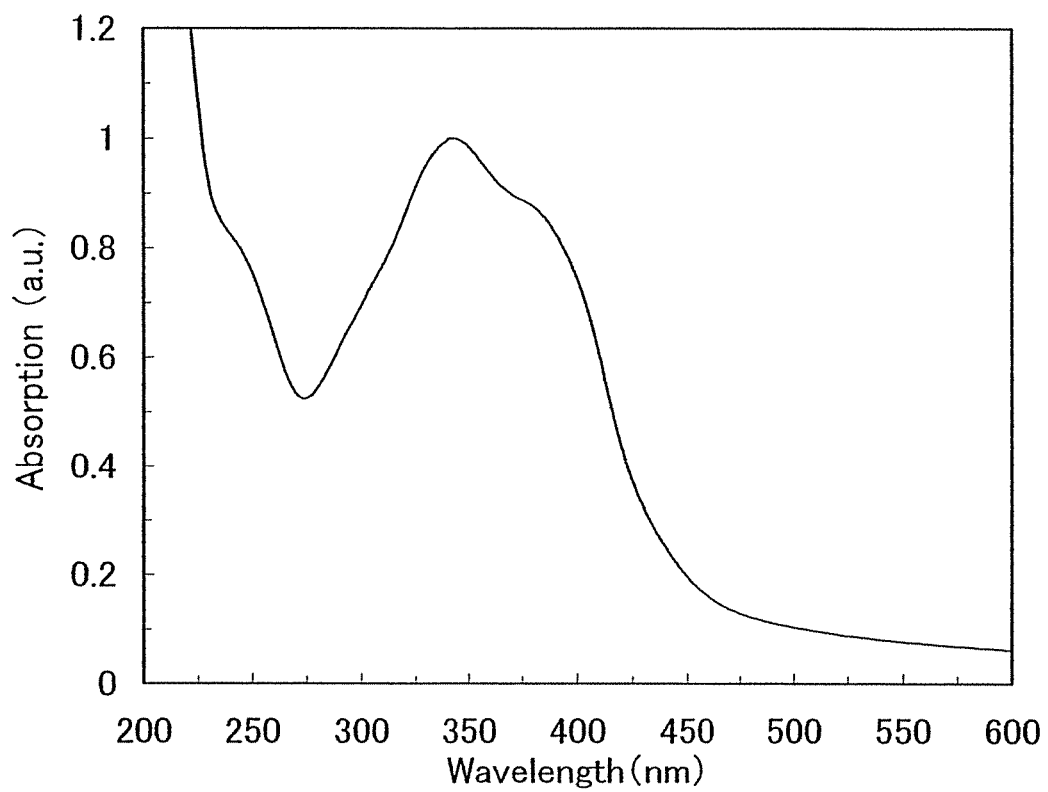
FIG. 8 is a graph showing an absorption spectrum in a thin film state of 4-[N-(4-biphenylyl)-N-phenylamino]stilbene which is a stilbene derivative of the present invention.

FIG. 7 shows an absorption spectrum of a toluene solution of BPAS. FIG. 8 shows an absorption spectrum of a thin film of BPAS. According to FIGS. 7 and 8, it was found that the peak was at 336 nm in the case of the toluene solution, and at 387 nm in the case of the thin film state.

Figure 9:
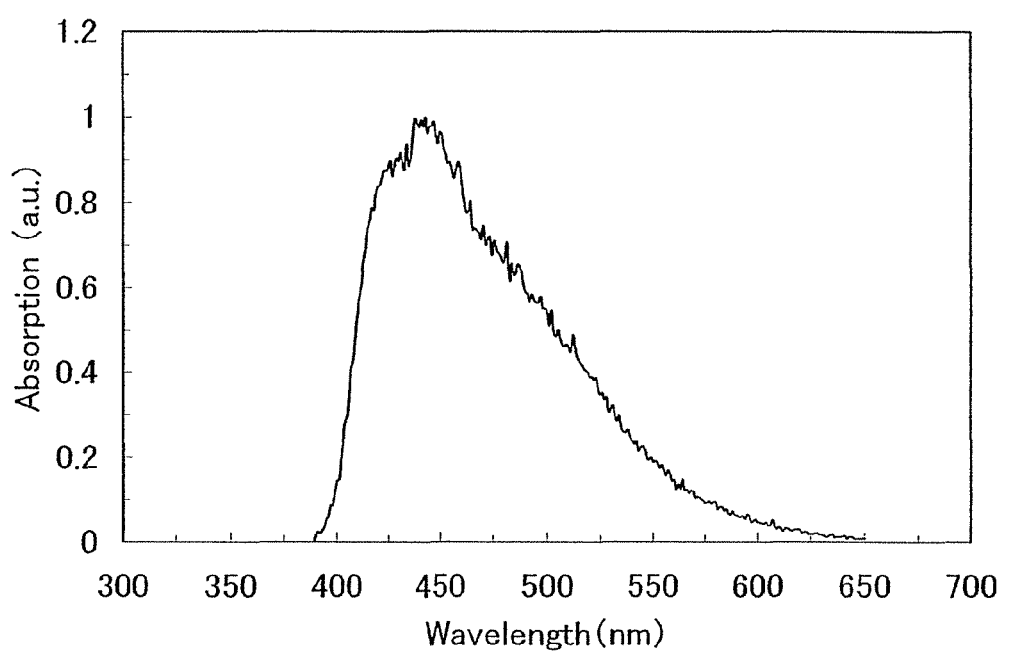
FIG. 9 is a graph showing an emission spectrum in a toluene solution of 4-[N-(4-biphenylyl)-N-phenylamino]stilbene is a stilbene derivative of the present invention.
Figure 10:
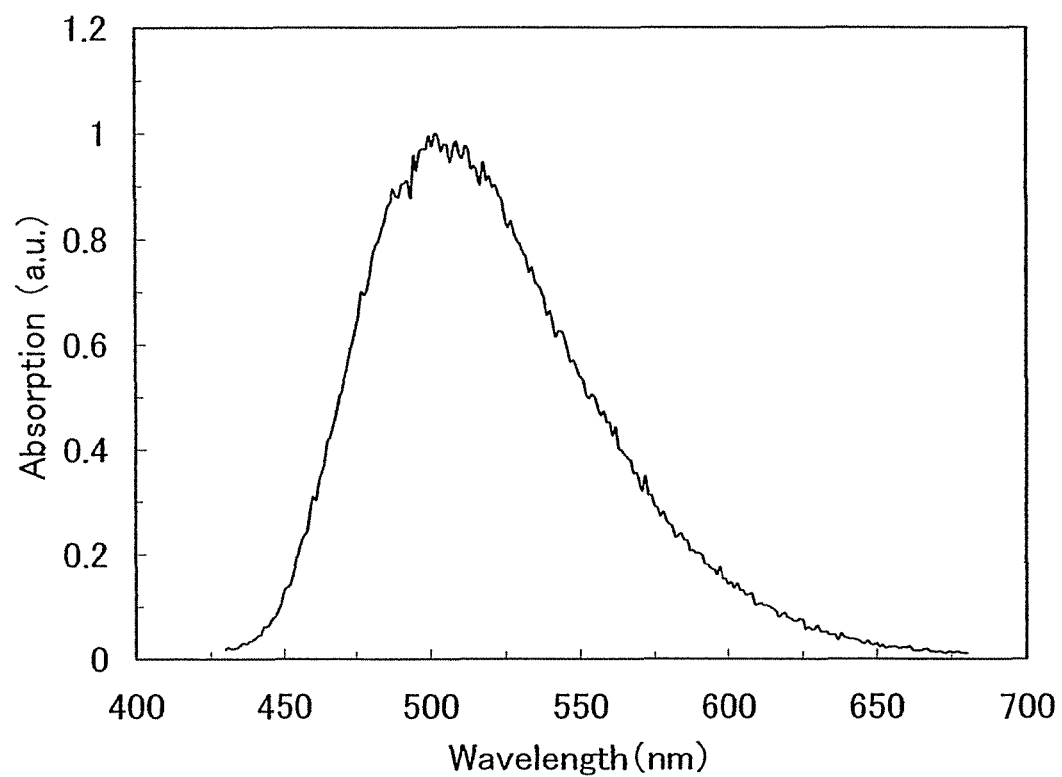
FIG. 10 is a graph showing an emission spectrum in a thin film state of 4-[N-(4-biphenylyl)-N-phenylamino]stilbene which is a stilbene derivative of the present invention.

FIG. 9 shows a light emission spectrum of the toluene solution of BPAS excited by UV light having a wavelength of 373 nm. According to FIG. 9, it is found that the light emission maximum was at approximately 483 nm in the toluene solution. FIG. 10 shows a light emission spectrum of a thin film (solid state) of BPAS excited by ultraviolet ray having a wavelength of 343 nm. According to FIG. 12, the light emission maximum was at 502 nm in the solid state.

A HOMO level in the thin film state is measured by photoelectron spectroscopy (AC-2, manufactured by Riken Keiki Co., Ltd.) in atmospheric air. The measurement result is −5.44 eV. Further, an optical energy gap is obtained from a Tauc plot assuming direct transition by using the data of the absorption spectrum in FIG. 8. The energy gap is 2.81 eV. Therefore, a LUMO level is −2.63 eV.

Example 2

Figure 15:
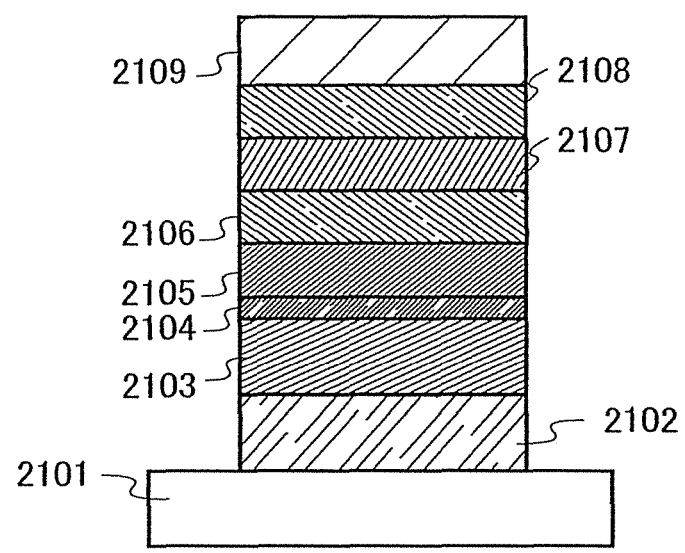
FIG. 15 illustrates a light-emitting element of the present invention.

Example 2 will describe a light-emitting element of the present invention with reference to FIG. 15. Chemical formulas of materials in this example are represented below.

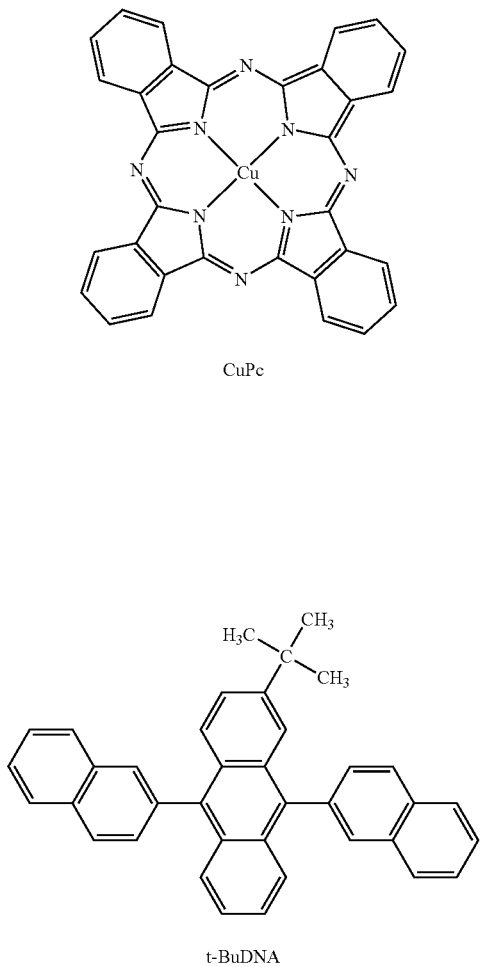

CuPc t-BuDNA

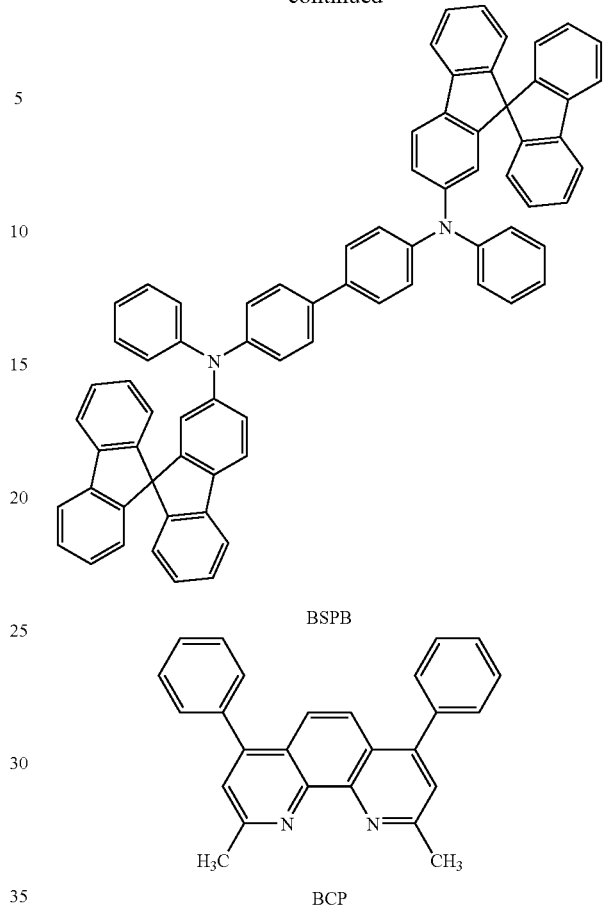

BSPB

BCP

A method for manufacturing of a light-emitting element in this example will be described below.

First, indium tin oxide including silicon oxide was formed over a glass substrate 2101 by a sputtering method to form a first electrode 2102. The first electrode 2102 has a film thickness of 110 nm and an electrode area of 2 mm×2 mm.

Next, the substrate over which the first electrode was formed was fixed to a substrate holder provided in a vacuum evaporation apparatus in such a way that a surface of the substrate having the first electrode faced downward. The inside of the vacuum evaporation apparatus was evacuated and the pressure was reduced to be about $10^{-4}$ Pa. Then, CuPc was formed to a thickness of 20 nm to form a hole-injecting layer 2103 over the first electrode 2102.

Subsequently, BSPB was formed to a thickness of 40 nm over the hole injecting layer 2103 by an evaporation method using resistance heating to form a hole-transporting layer 2104.

Further, (E)-4-[N-(4-biphenylyl)-N-phenylamino]stilbene (hereinafter referred to as BPAS) represented by structural formula (9), which is a stilbene derivative of the present invention and t-BuDNA were codeposited, thereby forming a light-emitting layer 2105 having a film thickness of 30 nm over the hole transporting layer 2104. Here, the weight ratio of t-BuDNA to BPAS was adjusted to be 1:0.1 (=t-BuDNA: BPAS).

Next, BCP was formed to a thickness of 20 nm over the light-emitting layer 2105 by vapor deposition using resistance heating, thereby forming a hole blocking layer 2106.

After that, an electron-transporting layer 2106 of BAlq having a thickness of 10 mm was formed over the light-emitting layer 2105 by an evaporation method using resistance heating.

Further, calcium fluoride ($CaF_2$) was formed to a thickness of 1 nm over the electron transporting layer 2107 to form an electron injection layer 2108.

Then, a second electrode 2109 having a thickness of 200 nm was formed of aluminum over the electron-injecting layer 2108 by an evaporation method using resistance heating. Thus, the light-emitting element of Example 2 was manufactured.

Figure 11:
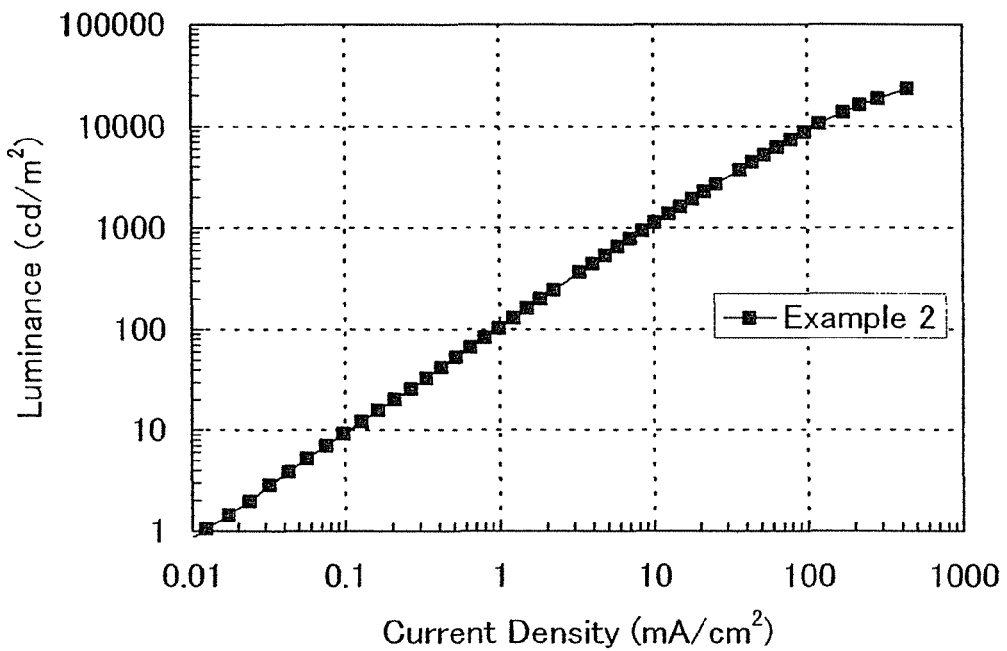
FIG. 11 is a graph showing luminance-current density characteristics of a light-emitting element in Example 2.
Figure 12:
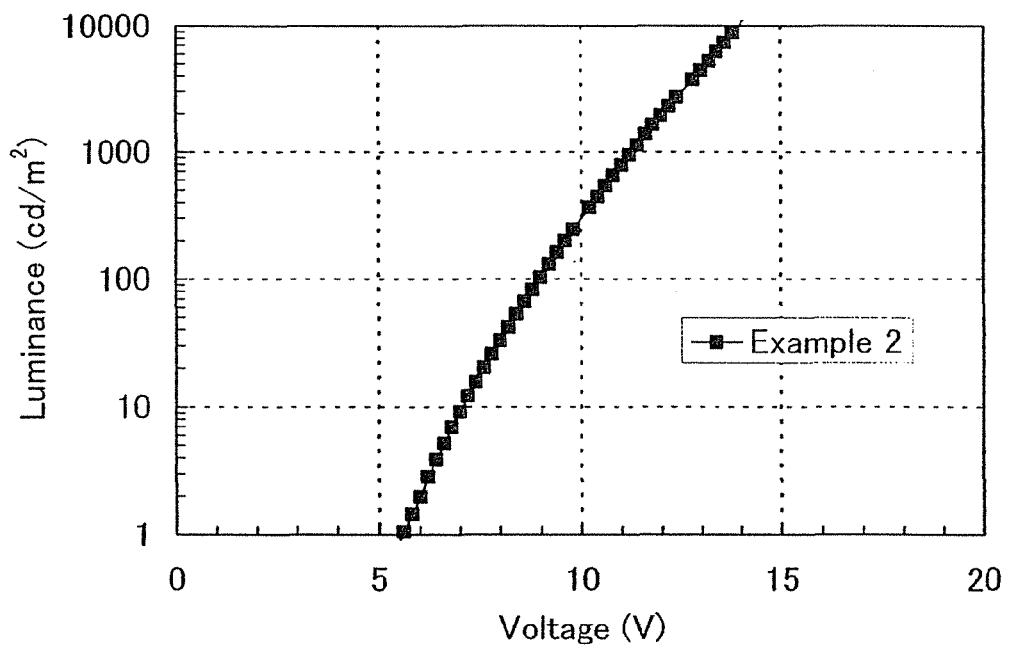
FIG. 12 is a graph showing luminance-voltage characteristics of the light-emitting element in Example 2.
Figure 13:
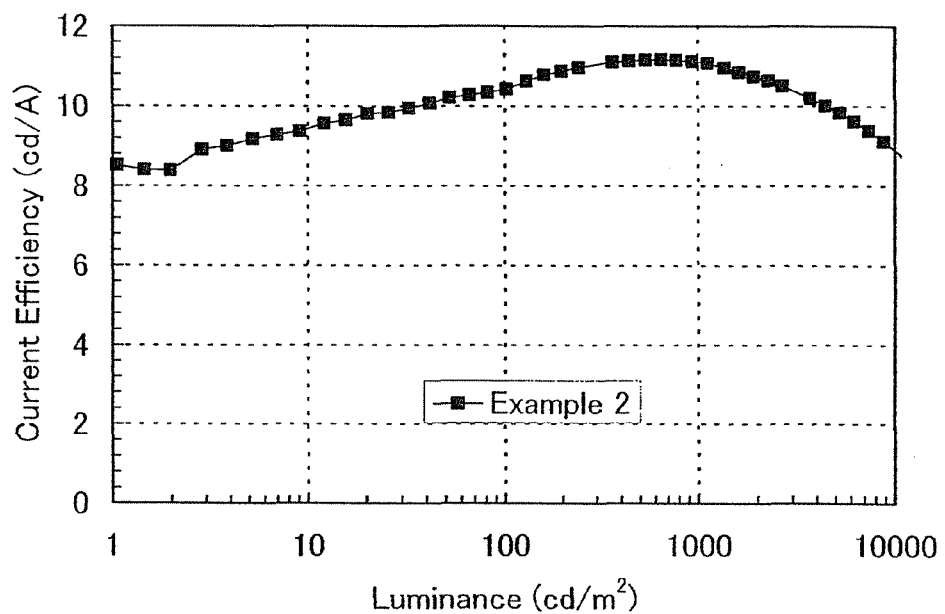
FIG. 13 is a graph showing current efficiency-luminance of the light-emitting element in Example 2.
Figure 14:
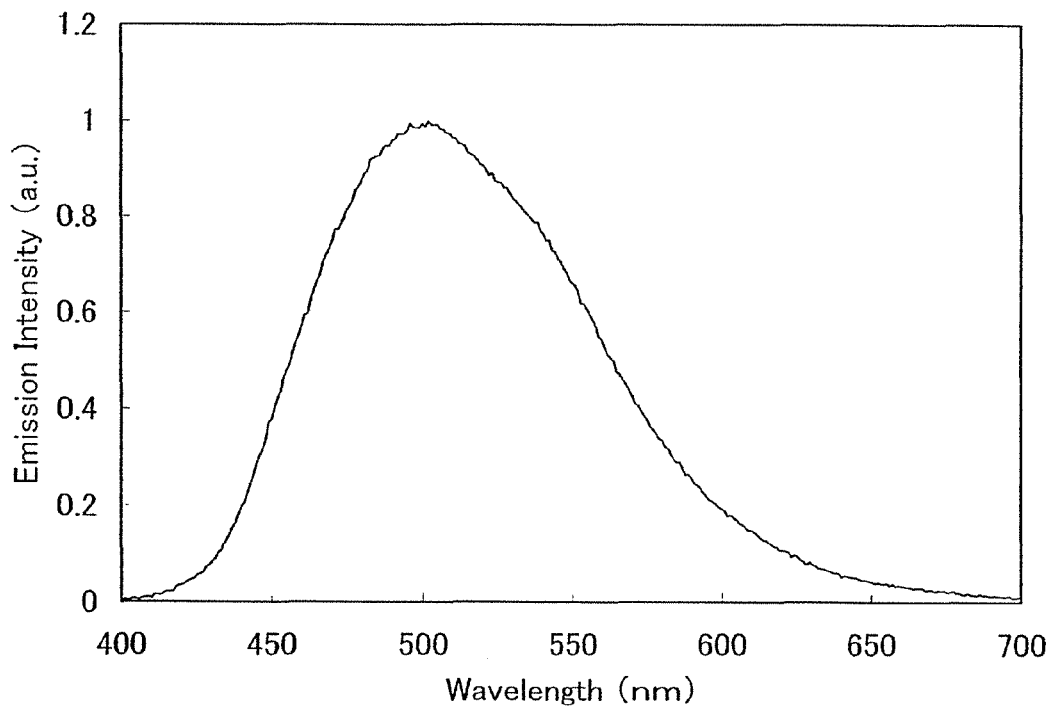
FIG. 14 is a graph showing an emission spectrum of the light-emitting element in Example 2.

FIGS. 11, 12, and 13 illustrate current density-luminance characteristics, voltage-luminance characteristics, and luminance-current efficiency of the light-emitting element in Example 2, respectively. FIG. 14 illustrates an emission spectrum when 1 mA of current flows. In the light-emitting element of Example 2, a voltage necessary to obtain luminance of 538 $cd/m^2$ was 10.6 V, and the current at that time was 0.19 mA (current density was 4.8 $mA/cm^2$), and the CIE chromaticity coordinates were (x=0.23, y=0.43). The current efficiency was 11 cd/A, and the power efficiency was 3.3 lm/W at that time.

A light emitting element of this example has high light emission efficiency. Therefore, a light emitting element with reduced power consumption was obtained.

Further, since a stilbene derivative of the present invention which has high heat resistance is used in the light emitting element of this example, heat resistance of the light emitting element was improved.

This application is based on Japanese Patent Application Serial No. 2006-265207 filed in Japan Patent Office on Sep. 28, 2006, the entire contents of which are hereby incorporated by reference.

What is claimed is:

1. A light-emitting element comprising:
a pair of electrodes; and
a light-emitting layer between the pair of electrodes,
wherein the light-emitting layer comprises a stilbene derivative expressed by a general formula (1),

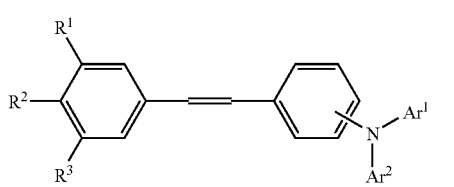

(1)

wherein $R^1$ to $R^3$ each represent a hydrogen atom or an alkyl group having 1 to 3 carbon atoms, and
wherein $Ar^1$ represents one of an unsubstituted biphenyl group or an unsubstituted terphenyl group, and $Ar^2$ represents one of an unsubstituted phenyl group, an unsubstituted biphenyl group, or an unsubstituted terphenyl group.

2. A light-emitting device comprising:
the light-emitting element according to claim 1; and
a controlling means for controlling light emission of the light-emitting element.

3. An electronic device comprising a display portion; wherein the display portion comprises the light-emitting element according to claim 1 and a controlling means for controlling light emission of the light-emitting element.

4. A light-emitting element comprising:
a pair of electrodes; and
a light-emitting layer between the pair of electrodes,
wherein the light-emitting layer comprises a stilbene derivative expressed by a general formula (2),

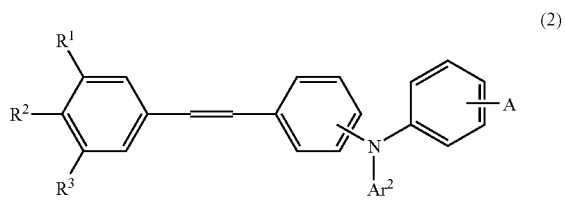

(2)

(3)

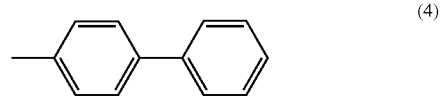

(4)

wherein $R^1$ to $R^3$ each represent a hydrogen atom or an alkyl group having 1 to 3 carbon atoms, and
wherein A represents a substituent expressed by the structural formula (3) or the structural formula (4), and $Ar^2$ represents one of an unsubstituted phenyl group, a substituted or unsubstituted biphenyl group, or a substituted or unsubstituted terphenyl group.

5. A light-emitting device comprising:
the light-emitting element according to claim 4; and
a controlling means for controlling light emission of the light-emitting element.

6. An electronic device comprising a display portion;
wherein the display portion comprises the light-emitting element according to claim 4 and a controlling means for controlling light emission of the light-emitting element.

7. A light-emitting element comprising:
a pair of electrodes; and
a light-emitting layer between the pair of electrodes,
wherein the light-emitting layer comprises a stilbene derivative expressed by a general formula (5),

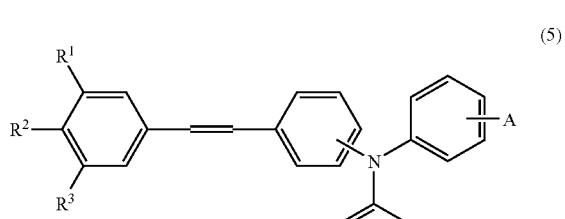

(5)

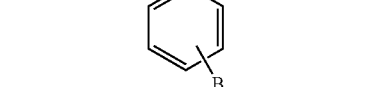

(6)

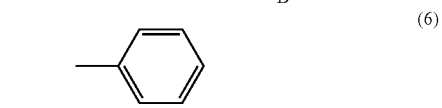

(7)

wherein $R^1$ to $R^3$ each represent a hydrogen atom or an alkyl group having 1 to 3 carbon atoms, and wherein A represents a substituent expressed by the structural formula (6) or the structural formula (7), and B represents a hydrogen atom or a substituent expressed by the structural formula (6) or the structural formula (7).

8. A light-emitting device comprising:

the light-emitting element according to claim 7; and a controlling means for controlling light emission of the light-emitting element.

9. An electronic device comprising a display portion;

wherein the display portion comprises the light-emitting element according to claim 7 and a controlling means for controlling light emission of the light-emitting element.

10. A light-emitting element comprising:

a pair of electrodes; and a light-emitting layer between the pair of electrodes, wherein the light-emitting layer comprises a stilbene derivative expressed by a general formula (8),

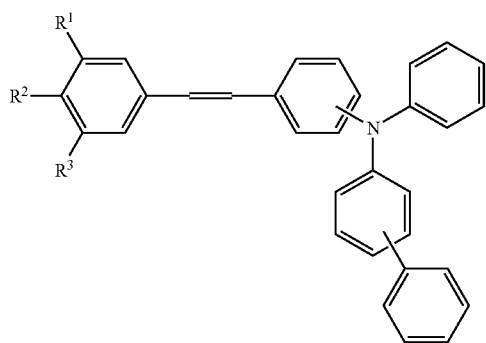

(8)

wherein $R^1$ to $R^3$ each represent a hydrogen atom, or an alkyl group having 1 to 3 carbon atoms.

11. A light-emitting device comprising:

the light-emitting element according to claim 10; and a controlling means for controlling light emission of the light-emitting element.

12. An electronic device comprising a display portion;

wherein the display portion comprises the light-emitting element according to claim 10 and a controlling means for controlling light emission of the light-emitting element.

13. A light-emitting element comprising:

a pair of electrodes; and a light-emitting layer between the pair of electrodes, wherein the light-emitting layer comprises a stilbene derivative expressed by a structural formula (9)

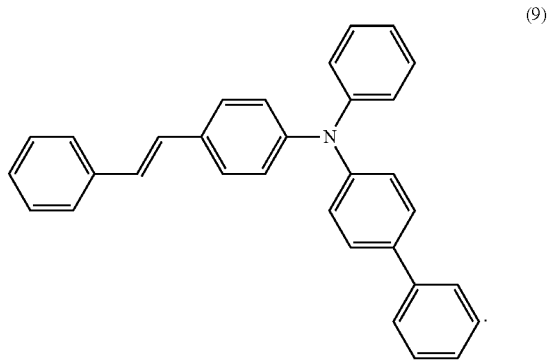 [SMILES: C(=C\c1ccc(N(c2ccccc2)c2ccc(-c3ccccc3)cc2)cc1)/c1ccccc1]

(9)

14. A light-emitting device comprising:

the light-emitting element according to claim 13; and a controlling means for controlling light emission of the light-emitting element.

15. An electronic device comprising a display portion;

wherein the display portion comprises the light-emitting element according to claim 13 and a controlling means for controlling light emission of the light-emitting element.

* * * * *

UNITED STATES PATENT AND TRADEMARK OFFICE
CERTIFICATE OF CORRECTION

PATENT NO. : 8,911,882 B2
APPLICATION NO. : 11/858544
DATED : December 16, 2014
INVENTOR(S) : Masakazu Egawa It is certified that error appears in the above-identified patent and that said Letters Patent is hereby corrected as shown below:

In the Specification:

Column 21, Lines 30 to 35; Change

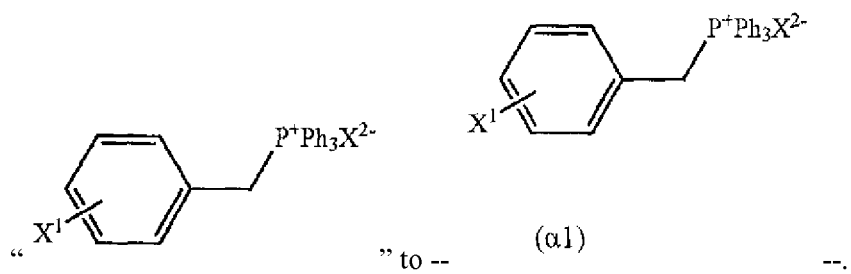

" to -- --.

Column 25, Lines 1 to 21; Change

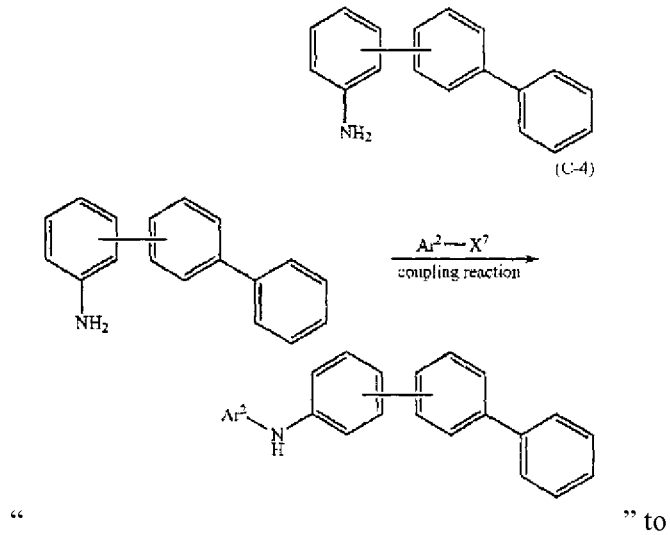

" to

Signed and Sealed this
Sixth Day of October, 2015

Michelle K. Lee
*Director of the United States Patent and Trademark Office*

CERTIFICATE OF CORRECTION (continued)
U.S. Pat. No. 8,911,882 B2

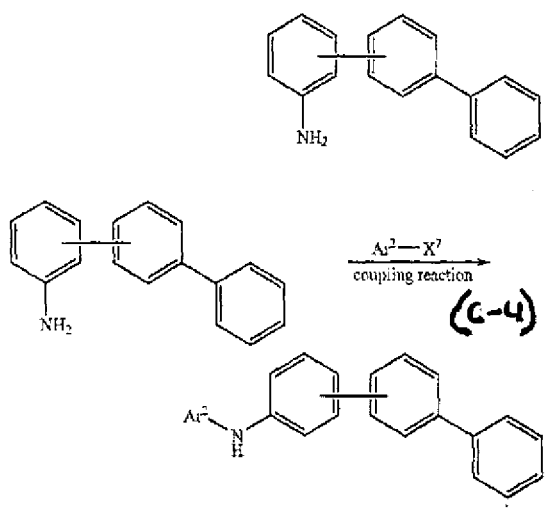

Column 28, Line 15; Change "cm$^2$ Vs" to --cm$^2$/Vs--.

Column 31, Line 21; Change "CzPA)-4,4'-di" to --CzPA) 4,4'-di--.

Column 40, Lines 1 to 25; Change

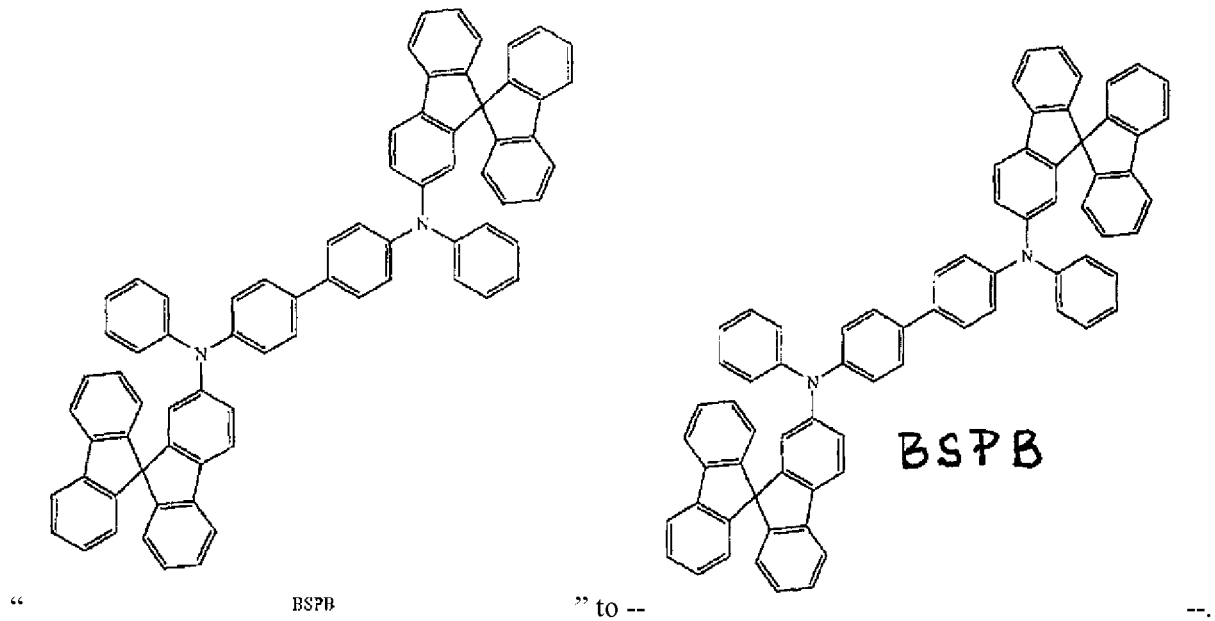

Column 41, Line 2; Change "10 mm" to --10 nm--.